(12) United States Patent
Noriega et al.

(10) Patent No.: US 7,628,763 B2
(45) Date of Patent: *Dec. 8, 2009

(54) GUIDEWIRE FOR CROSSING OCCLUSIONS OR STENOSES

(75) Inventors: Gerardo V. Noriega, Mountain View, CA (US); Victor Chechelski, Winterville, NC (US); Rudolfo Sudaria, Union City, CA (US)

(73) Assignee: Revascular Therapeutics, Inc., Sunnyvale, CA (US)

( * ) Notice: Subject to any disclaimer, the term of this patent is extended or adjusted under 35 U.S.C. 154(b) by 493 days.

This patent is subject to a terminal disclaimer.

(21) Appl. No.: 10/950,161

(22) Filed: Sep. 24, 2004

(65) Prior Publication Data

US 2005/0113853 A1 May 26, 2005

Related U.S. Application Data

(63) Continuation of application No. 09/644,201, filed on Aug. 22, 2000, now Pat. No. 6,824,550.

(60) Provisional application No. 60/195,154, filed on Apr. 6, 2000.

(51) Int. Cl.
*A61B 5/00* (2006.01)

(52) U.S. Cl. .................. 600/585; 604/22; 606/159

(58) Field of Classification Search ......... 606/113–114, 606/159, 167, 168, 170, 171, 180; 604/22, 604/523, 508; 600/585
See application file for complete search history.

(56) References Cited

U.S. PATENT DOCUMENTS

| | | | |
|---|---|---|---|
| 4,068,660 A | 1/1978 | Beck | |
| 4,368,730 A | 1/1983 | Sharrock | |
| 4,377,169 A | 3/1983 | Banks | |
| 4,445,509 A | 5/1984 | Auth | |
| 4,471,779 A | 9/1984 | Antoshkiw et al. | |
| 4,490,421 A | 12/1984 | Levy | |
| 4,516,972 A | 5/1985 | Samson | |
| 4,534,363 A | 8/1985 | Gold | |
| 4,538,622 A | 9/1985 | Samson et al. | |
| 4,545,390 A | 10/1985 | Leary | |
| 4,548,206 A | 10/1985 | Osborne | |
| 4,554,929 A | 11/1985 | Samson et al. | |
| 4,573,470 A | 3/1986 | Samson et al. | |
| 4,586,923 A | 5/1986 | Gould et al. | |
| 4,601,705 A | 7/1986 | McCoy | |
| 4,613,385 A | 9/1986 | Thomas et al. | |
| 4,616,653 A | 10/1986 | Samson et al. | |

(Continued)

OTHER PUBLICATIONS

International Search Report and Written Opinion of PCT Application No. PCT/US05/42763, dated Mar. 6, 2008, 13 pages total.

*Primary Examiner*—Michael J Milano
*Assistant Examiner*—Victor X Nguyen
(74) *Attorney, Agent, or Firm*—Townsend and Townsend and Crew LLP

(57) ABSTRACT

Systems and methods for crossing stenosis, partial occlusions, or complete occlusions within a body lumen. The systems generally include an elongate member such as a hollow guidewire that houses a rotatable and translatable drive shaft. The drive shaft typically has a distal portion that is advanced to create a path in the occlusive material that is large enough to allow the hollow guidewire to cross the occlusive material.

16 Claims, 22 Drawing Sheets

U.S. PATENT DOCUMENTS

| | | | |
|---|---|---|---|
| 4,619,263 A | 10/1986 | Frisbie et al. |
| 4,641,654 A | 2/1987 | Samson et al. |
| 4,646,719 A | 3/1987 | Neuman et al. |
| 4,646,742 A | 3/1987 | Packard et al. |
| 4,676,249 A | 6/1987 | Arenas et al. |
| 4,708,717 A | 11/1987 | Deane et al. |
| 4,708,718 A | 11/1987 | Daniels |
| 4,715,378 A | 12/1987 | Pope, Jr. et al. |
| 4,717,387 A | 1/1988 | Inoue et al. |
| 4,719,924 A | 1/1988 | Crittenden et al. |
| 4,721,117 A | 1/1988 | Mar et al. |
| 4,723,936 A | 2/1988 | Buchbinder et al. |
| 4,739,768 A | 4/1988 | Engelson |
| 4,763,647 A | 8/1988 | Gambale |
| 4,767,400 A | 8/1988 | Miller et al. |
| 4,779,628 A | 10/1988 | Machek |
| 4,781,486 A | 11/1988 | Mochizuki |
| 4,798,598 A | 1/1989 | Bonello et al. |
| 4,832,047 A | 5/1989 | Sepetka et al. |
| 4,846,186 A | 7/1989 | Box et al. |
| 4,899,787 A | 2/1990 | Ouchi et al. |
| 4,906,241 A | 3/1990 | Noddin et al. |
| 4,923,462 A | 5/1990 | Stevens |
| 4,925,445 A | 5/1990 | Sakamoto et al. |
| 4,926,858 A | 5/1990 | Gifford, III et al. |
| 4,940,062 A | 7/1990 | Hampton et al. |
| 4,946,466 A | 8/1990 | Pinchuk et al. |
| 4,953,553 A | 9/1990 | Tremulis |
| 4,979,939 A | 12/1990 | Shiber |
| 4,990,134 A | 2/1991 | Auth |
| 5,021,044 A | 6/1991 | Sharkawy |
| 5,030,204 A | 7/1991 | Badger et al. |
| 5,041,082 A | 8/1991 | Shiber |
| 5,041,085 A | 8/1991 | Osborne et al. |
| 5,059,851 A | 10/1991 | Corl et al. |
| 5,060,660 A | 10/1991 | Gambale et al. |
| 5,067,489 A | 11/1991 | Lind |
| 5,107,852 A | 4/1992 | Davidson et al. |
| 5,115,814 A | 5/1992 | Griffith et al. |
| 5,116,350 A | 5/1992 | Stevens |
| 5,144,959 A | 9/1992 | Gamble et al. |
| 5,165,421 A | 11/1992 | Fleischhacker et al. |
| 5,176,661 A | 1/1993 | Evard et al. |
| 5,178,158 A | 1/1993 | de Toledo |
| 5,184,627 A | 2/1993 | de Toledo |
| 5,195,971 A | 3/1993 | Sirhan |
| 5,209,727 A | 5/1993 | Radisch, Jr. et al. |
| 5,211,636 A | 5/1993 | Mische |
| 5,217,482 A | 6/1993 | Keith |
| 5,250,034 A | 10/1993 | Appling et al. |
| 5,267,979 A | 12/1993 | Appling et al. |
| 5,306,252 A | 4/1994 | Yutori et al. |
| 5,314,438 A | 5/1994 | Shturman |
| RE34,695 E | 8/1994 | Mar et al. |
| 5,345,945 A | 9/1994 | Hodgson et al. |
| 5,346,473 A | 9/1994 | Bowman |
| 5,358,485 A * | 10/1994 | Vance et al. | 604/22 |
| 5,368,035 A | 11/1994 | Hamm et al. |
| 5,377,690 A | 1/1995 | Berthiaume |
| 5,462,523 A | 10/1995 | Samson et al. |
| 5,484,407 A | 1/1996 | Osypka |
| 5,527,298 A | 6/1996 | Vance et al. |
| 5,527,326 A | 6/1996 | Hermann et al. |
| 5,569,197 A | 10/1996 | Helmus et al. |
| 5,571,085 A | 11/1996 | Accisano, III |
| 5,591,142 A | 1/1997 | Van Erp |
| 5,606,981 A | 3/1997 | Tartacower et al. |
| 5,611,777 A | 3/1997 | Bowden et al. |
| 5,632,755 A | 5/1997 | Nordgren et al. |
| 5,651,785 A | 7/1997 | Abela et al. |
| 5,662,671 A | 9/1997 | Barbut et al. |
| 5,681,336 A * | 10/1997 | Clement et al. | 606/159 |
| 5,702,373 A | 12/1997 | Samson |
| 5,772,609 A | 6/1998 | Nguyen et al. |
| 5,776,114 A | 7/1998 | Frantzer |
| 5,820,591 A | 10/1998 | Thompson et al. |
| 5,843,103 A | 12/1998 | Wulfman |
| 5,848,986 A | 12/1998 | Lundquist et al. |
| 5,860,938 A | 1/1999 | LaFontaine et al. |
| 5,865,800 A | 2/1999 | Mirarchi et al. |
| 5,868,685 A | 2/1999 | Powell et al. |
| 5,897,567 A | 4/1999 | Ressemann et al. |
| 5,908,395 A | 6/1999 | Stalker et al. |
| 6,001,112 A | 12/1999 | Taylor |
| 6,022,336 A | 2/2000 | Zadno-Azizi et al. |
| 6,050,972 A | 4/2000 | Zadno-Azizi et al. |
| 6,056,743 A * | 5/2000 | Ellis et al. | 606/15 |
| 6,059,767 A | 5/2000 | Noriega |
| 6,066,149 A | 5/2000 | Samson et al. |
| 6,068,623 A | 5/2000 | Zadno-Azizi et al. |
| 6,093,157 A | 7/2000 | Chandrasekaran |
| 6,143,009 A | 11/2000 | Shiber |
| 6,152,909 A | 11/2000 | Bagaoisan et al. |
| 6,156,046 A | 12/2000 | Passafaro |
| 6,179,851 B1 | 1/2001 | Barbut et al. |
| 6,183,432 B1 * | 2/2001 | Milo | 604/22 |
| 6,217,567 B1 | 4/2001 | Zadno-Azizi et al. |
| 6,258,052 B1 | 7/2001 | Milo |
| 6,299,622 B1 | 10/2001 | Snow |
| 6,312,438 B1 | 11/2001 | Adams |
| 6,355,014 B1 | 3/2002 | Zadno-Azizi et al. |
| 6,375,628 B1 | 4/2002 | Zadno-Azizi et al. |
| 6,482,221 B1 | 11/2002 | Hebert et al. |
| 6,500,130 B2 | 12/2002 | Kinsella et al. |
| 6,533,749 B1 | 3/2003 | Mitusina et al. |
| 6,585,717 B1 | 7/2003 | Wittenberger et al. |
| 6,602,264 B1 | 8/2003 | McGurckin |
| 6,652,508 B2 | 11/2003 | Griffin et al. |
| 6,743,208 B1 | 6/2004 | Coyle |
| 6,746,422 B1 | 6/2004 | Noriega et al. |
| 6,824,550 B1 * | 11/2004 | Noriega et al. | 606/159 |

* cited by examiner

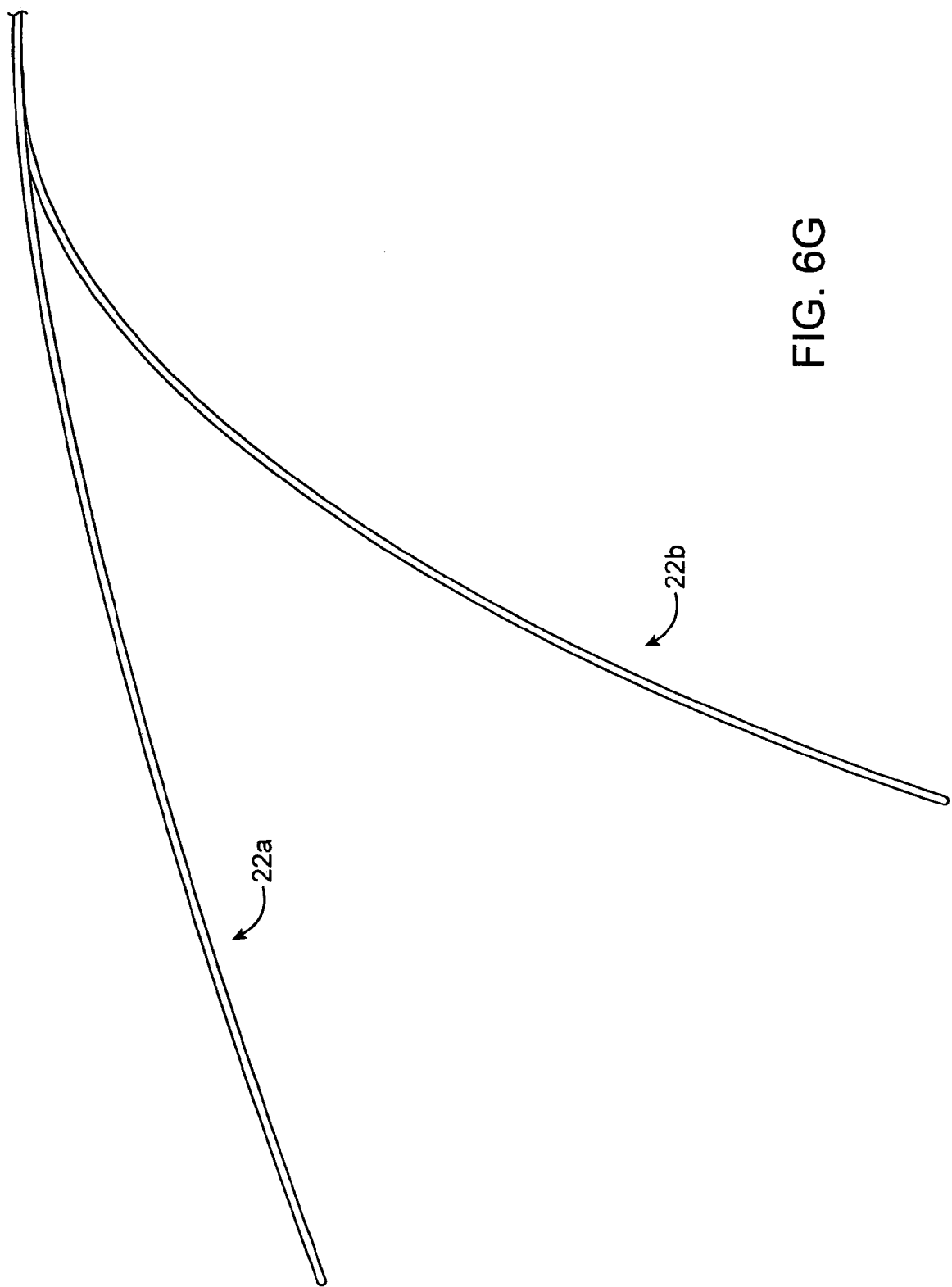

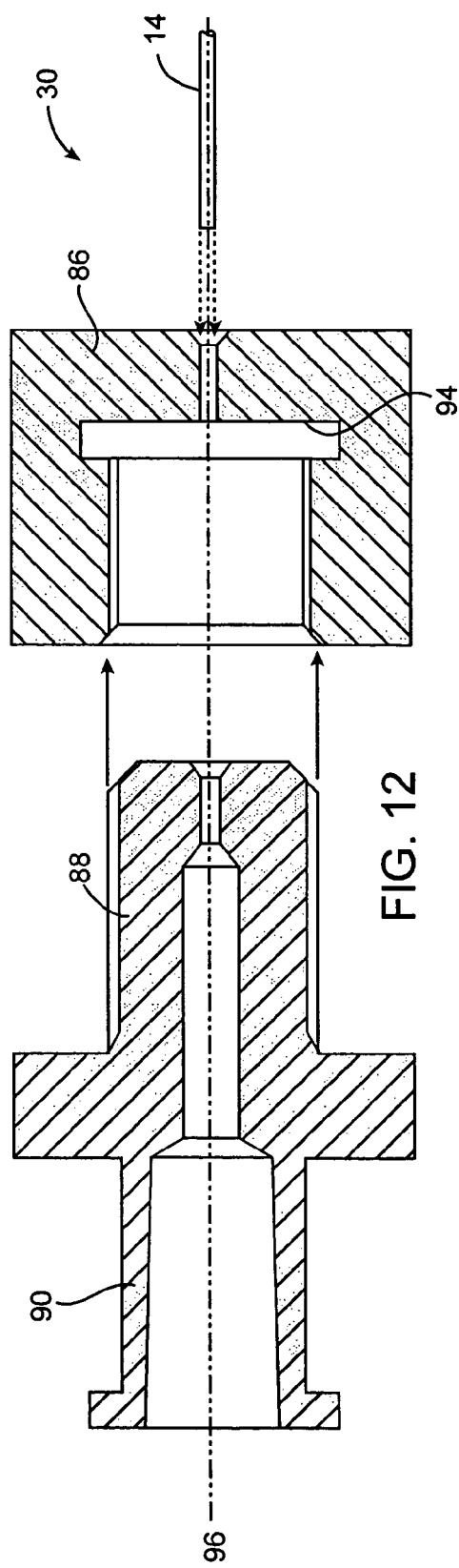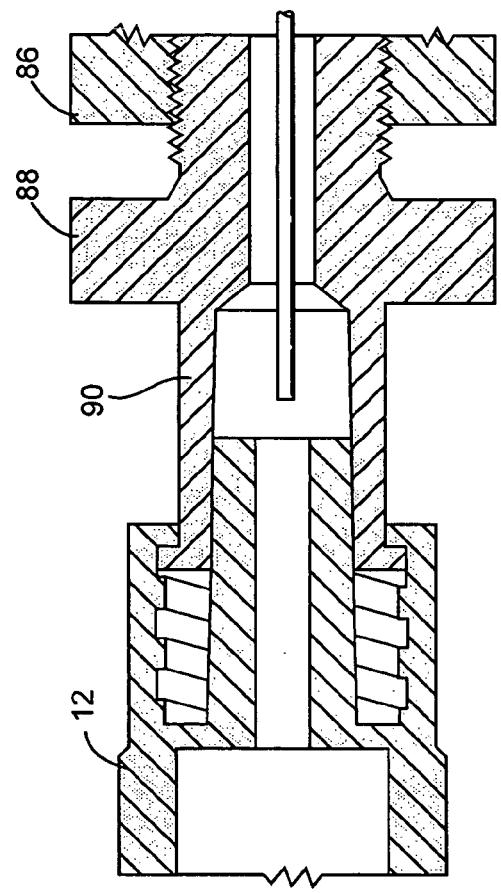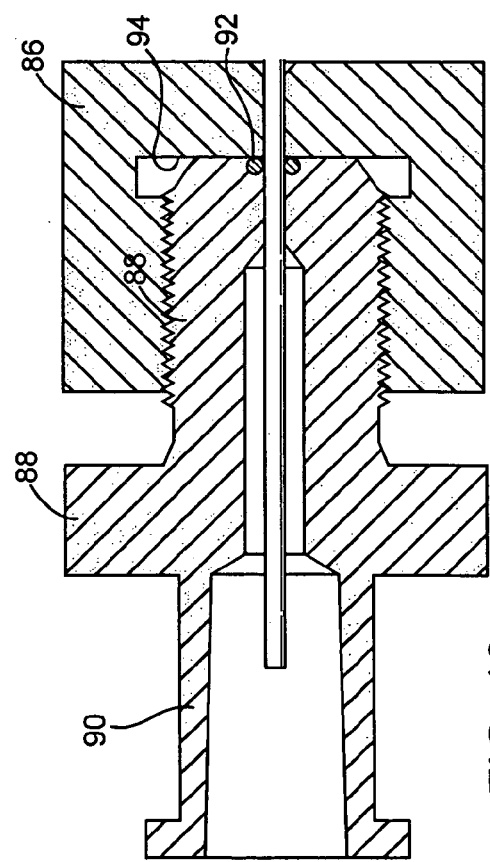
FIG. 12
FIG. 13
FIG. 14

GUIDEWIRE FOR CROSSING OCCLUSIONS OR STENOSES

CROSS-REFERENCES TO RELATED APPLICATIONS

The present application is a continuation application of U.S. patent application Ser. No. 09/644,201, filed Aug. 22, 2000, now U.S. Pat. No. 6,824,550, which claims benefit of U.S. Patent Application No. 60/195,154, filed Apr. 6, 2000, under 37 C.F.R. §1.78, the complete disclosures of which are incorporated herein by reference.

The present application is also related to U.S. patent application Ser. No. 09/030,657, filed Feb. 25, 1998, the complete disclosure of which is herein incorporated by reference.

BACKGROUND OF THE INVENTION

The present invention is generally related to medical devices, kits, and methods. More specifically, the present invention provides a system for crossing stenosis, partial occlusions, or total occlusions in a patient's body.

Cardiovascular disease frequently arises from the accumulation of atheromatous material on the inner walls of vascular lumens, particularly arterial lumens of the coronary and other vasculature, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging, but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Particular catheter-based interventions include angioplasty, atherectomy, laser ablation, stenting, and the like. For the most part, the catheters used for these interventions must be introduced over a guidewire, and the guidewire must be placed across the lesion prior to catheter placement. Initial guidewire placement, however, can be difficult or impossible in tortuous regions of the vasculature. Moreover, it can be equally difficult if the lesion is total or near total, i.e. the lesion occludes the blood vessel lumen to such an extent that the guidewire cannot be advanced across.

To overcome this difficulty, forward-cutting atherectomy catheters have been proposed. Such catheters usually can have a forwardly disposed blade (U.S. Pat. No. 4,926,858) or rotating burr (U.S. Pat. No. 4,445,509). While effective in some cases, these catheter systems, even with a separate guidewire, have great difficulty in traversing through the small and tortuous body lumens of the patients and reaching the target site.

For these reasons, it is desired to provide devices, kits, and methods which can access small, tortuous regions of the vasculature and which can remove atheromatous, thrombotic, and other occluding materials from within blood vessels. In particular, it is desired to provide atherectomy systems which can pass through partial occlusions, total occlusions, stenosis, and be able to macerate blood clots or thrombotic material. It is further desirable that the atherectomy system have the ability to infuse and aspirate fluids before, during, or after crossing the lesion. At least some of these objectives will be met by the devices and methods of the present invention described hereinafter and in the claims.

SUMMARY OF THE INVENTION

The present invention provides systems and methods for removing occlusive material and passing through occlusions, stenosis, thrombus, and other material in a body lumen. More particularly, the present invention can be used passing through stenosis or occlusions in a neuro, cardio, and peripheral body lumens. Generally, the present invention includes an elongate member that is positioned adjacent the occlusion or stenosis. A drive shaft having a distal tip is rotated and advanced from within the elongate member to create a path forward of the elongate member to form a path in the occlusion or stenosis. To facilitate passing through the occlusion or stenosis, the distal end of the elongate member can be steerable to provide better control the creation of the path through the occlusion or stenosis. Optionally, the target site can be infused and/or aspirated before, during, and after creation of the path through the occlusion.

In an exemplary embodiment, the elongate member is a hollow guidewire that has a flexibility, pushability and torqueability to be advanced through the tortuous blood vessel without the use of a separate guidewire. Additionally, the hollow guidewire may be sized to fit within a conventional support or access catheter system and inserted into the blood vessel and delivered to the target site. The catheter system can be delivered either concurrently with the advancement of the hollow guidewire or after the guidewire has reached the target site. The position of the hollow guidewire and catheter system can be maintained and stabilized while the drive shaft is rotated and translated out of the axial lumen of the hollow guidewire. The distal tip of the drive shaft can be deflected, coiled, blunted, flattened, enlarged, twisted, basket shaped, or the like. In some embodiments, to increase the rate of removal of the occlusive material, the distal tip is sharpened or impregnated with an abrasive material such as diamond chips, diamond powder, glass, or the like.

The drive shaft can be a counter-wound guidewire construction or be of a composite structure consisting of a fine wire around which a coil is wrapped. The counter-wound or composite constructions are more flexible than a single wire drive shaft and can provide a tighter bending radius while still retaining the torque transmitting ability so that it can still operate as a lesion penetration mechanism.

In a specific configuration, the drive shaft has spiral threads or external riflings extending along the shaft. The spirals typically extend from the proximal end of the shaft to a point proximal of the distal tip. As the drive shaft is rotated and axially advanced into the occlusive material, the distal tip creates a path and removes the material from the body. The rotating spirals act similar to an "Archimedes Screw" and transport the removed material proximally up the lumen of the elongate member and prevent the loose atheromatous material from escaping into the blood stream.

Systems and kits of the present invention can include a support system or access system, such as a catheter or guidewire having a body adapted for intraluminal introduction to the target blood vessel. The dimensions and other physical characteristics of the access system body will vary significantly depending on the body lumen which is to be accessed. In the exemplary case, the body of the support or access system is very flexible and is suitable for introduction over a conventional guidewire or the hollow guidewire of the present invention. The support or access system body can either be for "over-the-wire" introduction or for "rapid exchange," where the guidewire lumen extends only through a distal portion of the access system body. Optionally, the support or access system can have at least one axial channels extending through the lumen to facilitate infusion and/or aspiration of material from the target site. Support or access system bodies will typically be composed of an organic polymer, such as polyvinylchloride, polyurethanes, polyesters, polytetrafluoroethylenes (PTFE), silicone rubbers, natural rubbers, or the like. Suitable bodies may be formed by extrusion, with one or more lumens that extend axially through the body. For example, the support or access system can be a support catheter, interventional catheter, balloon dilation catheter, atherectomy catheter, rotational catheter, extractional catheter, laser ablation catheter, guiding catheter, stenting catheter, ultrasound catheter, and the like.

In other embodiments, a hollow guidewire can be used as the support or access system. The hollow guidewire can be navigated to and positioned at the target site, with or without the use of a separate guidewire. The hollow guidewire support system provides the flexibility, maneuverability, torqueability (usually 1:1), and columnar strength necessary for accurately advancing through the tortuous vasculature. The hollow guidewire support system can act as a working channel inside of which other interventional devices can be delivered to the target site. Such devices include, but are not limited to a rotating guidewire, infusion guidewire, clot maceration guidewire, normal guidewire, and the like. Because the hollow guidewire is not composed of polymer, the hollow guidewire working channel does not soften at body temperatures.

The hollow guidewire working channel typically has a thin wall construction which allows the lumen of the working channel to be maximized when compared with polymeric based catheter designs. This allows larger diameter devices to be inserted into it than can be inserted through similar sized catheter-based devices. The larger lumen of the hollow guidewire working channel allows devices such as clot macerators and other larger devices to be delivered to the target lesion. Additionally, the larger diameter lumen allows infusion or clot dissolving fluid and/or aspiration of the debris created in the clot maceration process.

In use, the access system can be delivered to the target site over a conventional guidewire. Once the access system has been positioned near the target site, the conventional guidewire can be removed and the elongate member can be advanced through the access system to the target site. Alternatively, because the elongate member can have the flexibility, pushability, and torqueability to be advanced through the tortuous regions of the vasculature, it is possible to advance the elongate member through the vasculature to the target site without the use of a separate guidewire. The access system can be advanced over the elongate member to the target site. Once the elongate member has been positioned at the target site, the drive shaft is rotated and advanced into the occlusive material. The rotation of the distal tip creates a path forward of the elongate member. In some embodiments the path created by the distal tip has a path radius which is larger than the radius of the distal end of the elongate member. In other embodiments, the path created by the distal tip has a path radius which is the same size or smaller than the radius of the elongate member.

One exemplary system for crossing an occlusion or stenosis within a body lumen comprises a drive shaft that is rotatably and translatably received within an axial lumen of an elongate member. Means at a distal portion of the drive shaft creates a path in front of the elongate member to facilitate crossing of the occlusion or stenosis. The means is moveable between an axially retracted configuration and an axially extended configuration. The means in the axially extended configuration creates a profile that is at least as large as the diameter of the distal end of the elongate member. In alternative implementations, the path creating means can move from the retracted position to an extended configuration that has a profile with the same or smaller profile than the distal end of the elongate member.

In another aspect, the present invention provides a system for crossing an occlusion or stenosis within a body lumen. The system comprises an elongate member having a proximal end, a distal end, and a lumen. A drive shaft is rotatably and translatably disposed in the elongate member and is removably attached to a rotating mechanism. The rotating mechanism rotates the drive shaft so that a distal tip can be advanced beyond the distal end of the elongate member to create a path through the occlusion or stenosis such that the elongate member can be advanced past the occlusion or stenosis. In a specific implementation, the rotating mechanism can be detached from the drive shaft and an access system can be delivered to the target site over the elongate member. Thereafter, the rotating mechanism can be reattached and the drive shaft can be rotated.

In yet another aspect, the present invention provides an assembly for crossing an occlusive or stenotic material in a body lumen. The assembly comprises a guidewire having an axial lumen. A drive shaft rotatably and translatably extends through the axial lumen of the guidewire. The drive shaft has a distal tip that can be rotated and advanced to create a path through the occlusive or stenotic material. In some embodiments, the guidewire has an outer diameter or periphery similar to conventional passive guidewires used for neuro, cardio, and peripheral interventions. The outer diameter or periphery of the guidewire having an axial lumen is typically between approximately 0.040 inches and 0.009 inches, and preferably between approximately 0.024 inches and 0.009 inches, and typically between 0.013 and 0.014 inches. Depending on the body lumen that is accessed, the outer diameter of the guidewire can be larger or smaller. In most embodiments, the guidewire has the torqueability, pushability, and steerability to be advanced through the body lumen.

In yet another aspect the present invention provides a guidewire system for passing through occlusions or stenosis. The system comprises a hollow guidewire having a distal end, a proximal end, and a lumen. A drive shaft is movably disposed within the hollow guidewire such that a distal tip portion can extend beyond the distal end of the hollow guidewire. A rotating mechanism can rotate the drive shaft and an actuator can be used to control the axial movement of the drive shaft. Activation of the actuator moves the distal end of the rotating drive shaft along its longitudinal axis to create a path through the occlusion or stenosis.

In yet another aspect, the present invention provides a method of crossing an occlusion or stenosis within a body lumen. The method comprises positioning an elongate member and a drive shaft in the body lumen. The drive shaft is rotated. The drive shaft is expanded from a retracted configuration to an expanded configuration. In the expanded configuration, the drive shaft creates a path that is at least as large as the perimeter of the distal end of the elongate member. The distal portion of the drive shaft is then advanced into the occlusion or stenosis to create a path in the occlusion or stenosis.

In another aspect the present invention provides a method of crossing an occlusion or stenosis within a body lumen. The method comprises advancing a guidewire through the body lumen. An access or support system is moved over the guidewire to the occlusion or stenosis. The guidewire is removed from the body lumen and a steerable elongate member having a drive shaft is passed through the lumen of the access system. The drive shaft is rotated within a lumen of the elongate member. The drive shaft is advanced from a retracted position to an extended position to create a path through the occlusion or stenosis.

In yet another aspect, the present invention provides a method of passing through an occlusive or stenotic material in a body lumen. The method comprises positioning a hollow guidewire with a drive shaft adjacent the occlusion. A drive shaft is rotated and advanced out of the hollow guidewire and into the occlusive or stenotic material to create a path through the occlusive or stenotic material. In some embodiments, the guidewire can then be moved through the occlusive or stenotic material and an access system can be positioned in the path through the occlusive or stenotic material. The remaining occlusive or stenotic material can then removed with the access system.

In another aspect, the present invention provides a kit. The kit has a hollow guidewire having a lumen. A rotatable drive shaft having a shaped distal tip is removably received within the lumen of the hollow guidewire. Instructions for use in passing occlusions or stenosis in a body lumen comprise rotating the inner wire within the steerable hollow guidewire and advancing the drive shaft into the occlusive or stenotic material to create a path through the occlusive or stenotic material. A package is adapted to contain the hollow guidewire, rotatable wire, and the instructions for use. In some embodiments, the instructions can be printed directly on the package, while in other embodiments the instructions can be separate from the package.

These and other aspects of the invention will be further evident from the attached drawings and description of the invention.

BRIEF DESCRIPTION OF THE DRAWINGS

FIG. 6G shows the relative flexibility between a conventional drive shaft and a counter-wound drive shaft of the present invention;

FIGS. 12-14 show a luer connection assembly which couples the elongate member to the housing;

DESCRIPTION OF THE SPECIFIC EMBODIMENTS

The systems, devices and methods according to the present invention will generally be adapted for the intraluminal treatment of a target site within a body lumen of a patient, usually in a coronary artery or peripheral blood vessel which is occluded or stenosed with atherosclerotic, stenotic, thrombotic, or other occlusive material. The systems, devices and methods, however, are also suitable for treating stenoses of the body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed at passing through atheromatous or thrombotic occlusive material in a coronary artery, it will be appreciated that the systems and methods of the present invention can be used to remove and/or pass through a variety of occlusive, stenotic, or hyperplastic material in a variety of body lumens.

Figure 1A:
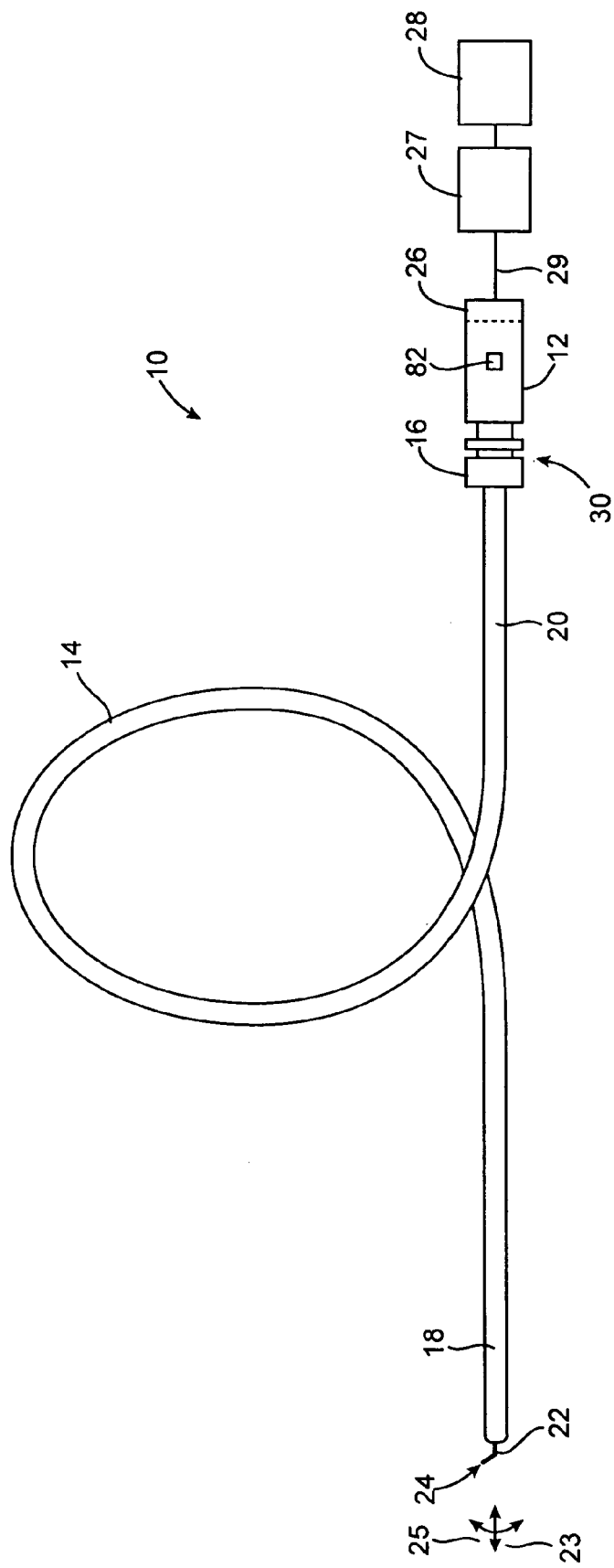
FIG. 1A shows an elevational view of a system of the present invention.

An apparatus 10 embodying features of the present invention is illustrated in FIG. 1A. The apparatus 10 generally includes a housing 12 coupled to an elongate member 14 which has a proximal end 16, a distal end 18, and an axial lumen 20. As shown by arrows 23, 25, the drive shaft 22 is movably received within the axial lumen 20 of the elongate member 14. The distal tip 24 of the drive shaft 22 has a shaped profile such that movement of the drive shaft creates a path forward of the distal end of the elongate member 14 for passing through the occlusive or stenotic material. In most configurations, wires 29 couple the drive motor 26 to the control system 27 and power supply 28. In some embodiments, the power supply 28 is covered with a plastic sheath cover so as to maintain a sterile environment (not shown).

The drive motor 26 is attachable to the proximal end of the drive shaft 14 to move (i.e., rotate, translate, reciprocate, vibrate, or the like) the drive shaft 22 and shaped distal tip 24. An input device 82 is attached to the housing 12 to control the rotation and/or axial movement of the drive shaft 22. The proximal end 16 of elongate member 14 is coupled to the housing 12 through a connector assembly 30. The connector assembly limits the motion of the elongate member 14 while allowing the drive shaft 22 to rotate and translate within the elongate member 14. Optionally, some embodiments of the connector assembly 30 includes an aspiration or infusion port (not shown) for facilitating fluid exchange (e.g., delivery or removal) at the target site.

Figure 1B:
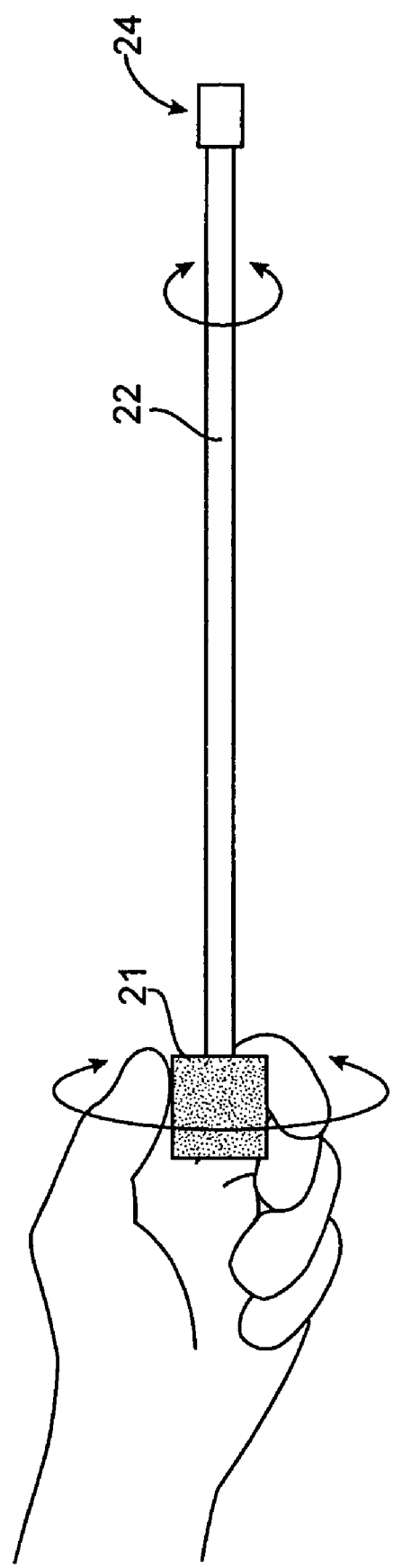
FIG. 1B shows manual manipulation of the drive shaft.

As shown in FIG. 1B, in order to macerate clots and to penetrate soft lesions, some drive shafts of the present invention can be configured to be manually rotated. In such embodiments, the proximal end of the drive shaft 22 can be grasped between the fingers and manually turned to rotate the distal tip 24. The proximal end can be optionally fit with a knurled knob 21 or other mechanism which allows manual manipulation of the proximal end of the drive shaft 22.

Figure 2:
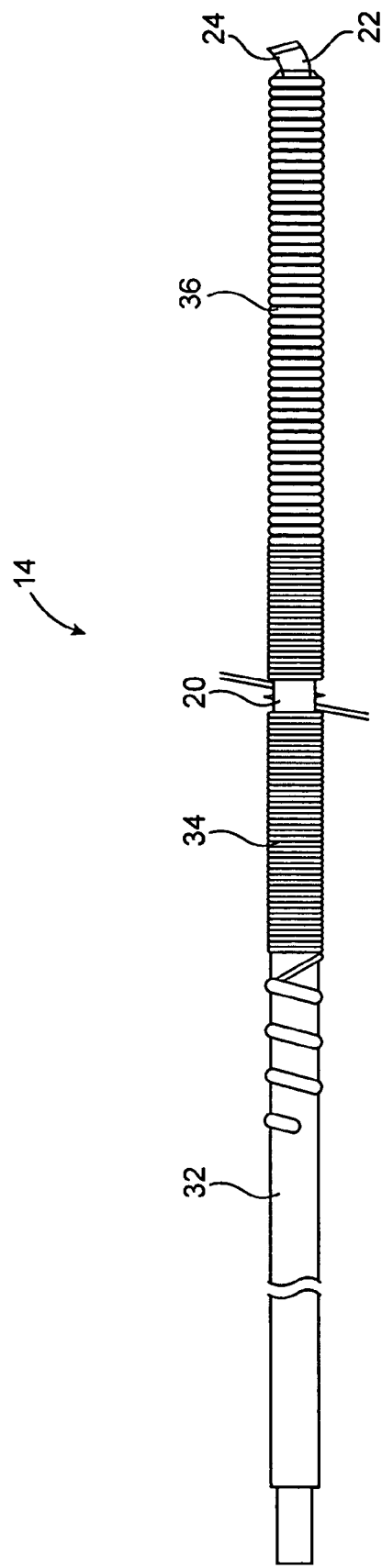
FIG. 2 shows a distal end of the elongate member and a distal tip of a drive shaft of the present invention.
Figure 3:
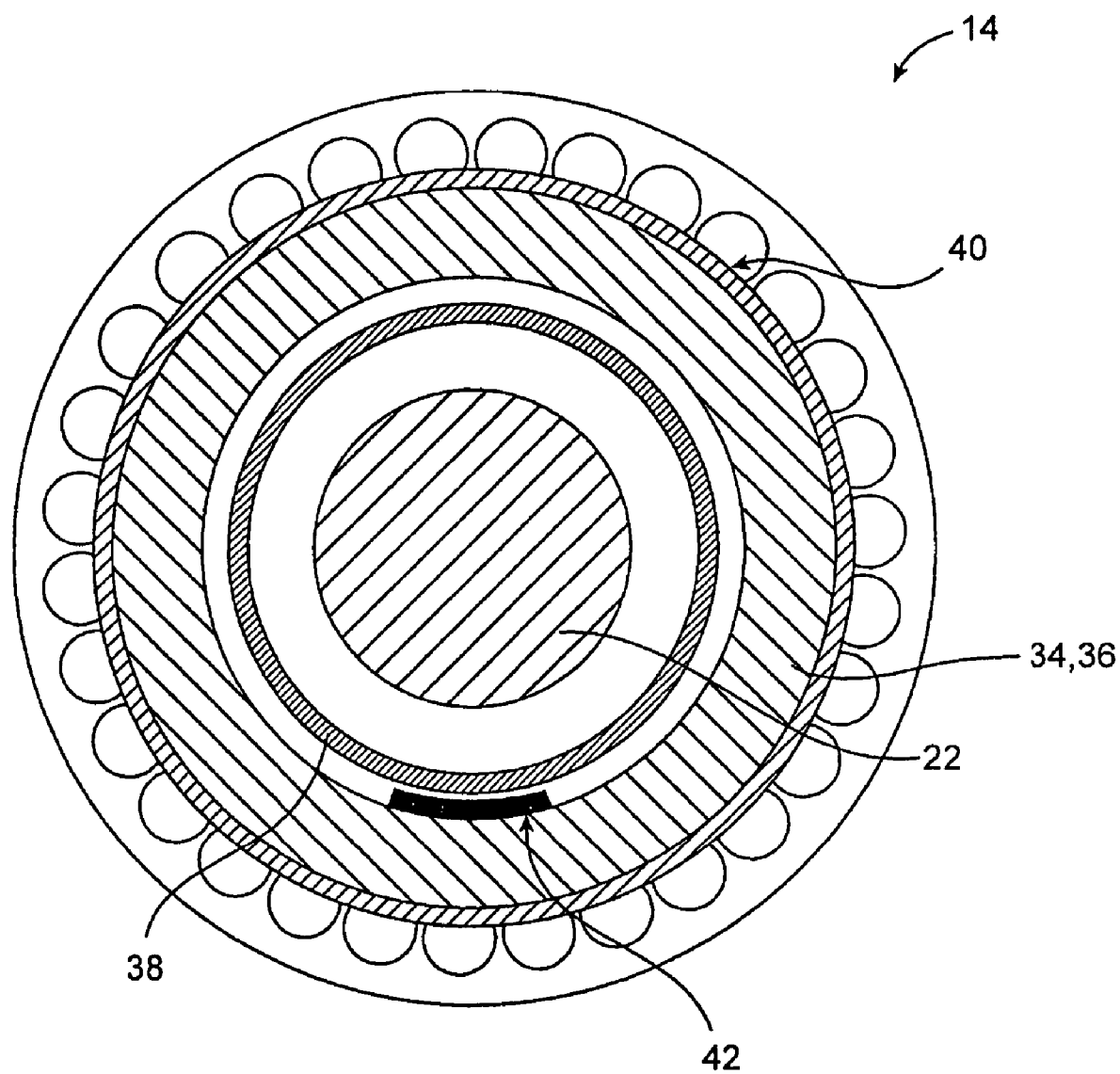
FIG. 3 is a cross sectional view of the device along A-A of FIG. 2.
Figure 4:
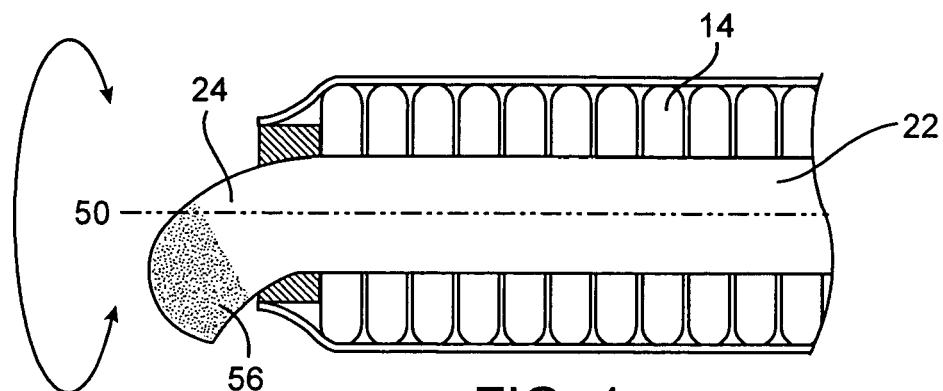
FIG. 4 shows a diamond chip embedded distal tip of the drive shaft.

An exemplary embodiment of the elongate member 14 is best seen in FIGS. 2 and 3. The elongate member 14 is preferably a flexible, hollow guidewire that has the flexibility, pushability, and torqueability to allow a user to advance the hollow guidewire directly through a tortuous blood vessel to the target site. Because of the high columnar strength of the hollow guidewire 14 there is typically no need for a separate guidewire.

In the exemplary embodiment illustrated in FIG. 2, the hollow guidewire has an helically wound elongated shaft which defines an axial lumen 20 that receives the drive shaft 22. The axial lumen 20 may further be used for infusion or aspiration. The hollow guidewire 14 includes a proximal tube 32, an intermediate coil 34, and a distal coil tip 36. In some embodiments the intermediate coil 34 is made of a stainless steel or nitinol coil, while the distal coil tip 36 is composed of a flexible, radiopaque coil, such as platinum-iridium. As shown, the intermediate coil 34 is threadedly engaged with the proximal tube 32 and distal tip 36, but it will be appreciated that the intermediate coil 34 can be connected to the proximal tube 32 and distal tip 36 by any conventional means, e.g. solder, adhesive, or the like. The proximal tube 32 of the hollow guidewire 14 can be coupled to a vacuum source or a fluid source (not shown) such that the target site can be aspirated or infused during the procedure, if desired.

Hollow guidewire 14 is typically sized to be inserted through coronary, neuro, or peripheral arteries and can have a variety of diameters. The outer diameter of the hollow guidewire is typically between approximately 0.009 inches and 0.040 inches and preferably between approximately 0.009 inches and 0.024 inches so as to ensure compatibility with existing interventional cardiology catheters and stent systems. The length of the hollow guidewire 14 may be varied to correspond to the distance between the percutaneous access site and the target site. For example, for a target site within the heart that is being accessed through the femoral artery, the hollow guidewire will typically have a length of approximately 175 cm. It should be noted however, that other embodiments of the hollow guidewire 14 may have dimensions that are larger or smaller than the above described embodiments and the present invention is not limited to the above recited dimensions.

Referring now to FIG. 3, a cross section of one embodiment of the hollow guidewire 14 is shown. An inner tube 38 and outer tube 40 are positioned around coils 34, 36 to provide a flexible, structural support which prevents liquids from moving between the blood vessel and the axial lumen of the elongate member 14. A reinforcing wire 42 can be positioned between the inner tube 38 and the coils 34, 36 to provide for deflection or steering of the distal end 18. The reinforcing wire 42 can be formed of a material having sufficient strength so that a thin profile is possible. For example, the reinforcing wire can be an at least partially flattened strip of stainless steel that can retain its shape until it is re-shaped to a different configuration. In one configuration, the reinforcing wire 42 is soldered or otherwise connected to the distal end of coil 36 and the remainder of the reinforcing wire 42 extends proximally to the housing 12. Manipulation of the proximal end of the reinforcing wire 42 allows the user to deflect or steer the distal tip 18 without permanently impairing the inner structure of the hollow guidewire 14. The steerable distal tip provides a user with greater intraluminal control of removing the occlusive or stenotic material from the blood vessel and also aids in navigating the hollow guidewire to the target site. In another configuration, the reinforcing wire is 42 can be soldered or otherwise connected to both the distal end and to the junction between coils 34, 36. Therefore, if the coils 34, 36, break, the attached reinforcing wire 42 can prevent the coils 34, 36 from detaching from the system 10. A more complete description of the hollow guidewire can be found in commonly owned U.S. patent application Ser. No. 09/030,657, filed Feb. 25, 1998, the complete disclosure of which was previously incorporated by reference.

FIGS. 4-9 show various embodiments of the drive shaft 22 of the present invention. In most embodiments, the drive shaft 22 is a wire, a counter-wound multiple strand wire, or a plurality of braided wires having a body 44 and a shaped distal tip 24. The proximal end of the drive shaft 22 can be removably coupled to a rotatable motor shaft 48 (FIGS. 10 and 11A) or manually manipulated (FIG. 1B). The body 44 of the drive shaft 22 extends through the elongate member 14 so that the distal tip 24 of the drive shaft is positioned near the distal end of the elongate member 14. The detachable connection to the motor shaft 48 allows the drive shaft 22 and elongate member 14 to be detached from the motor shaft 48 and connector assembly 30 so that an access or support system can be placed over the elongate member and advanced through the body lumen.

Figure 5A:
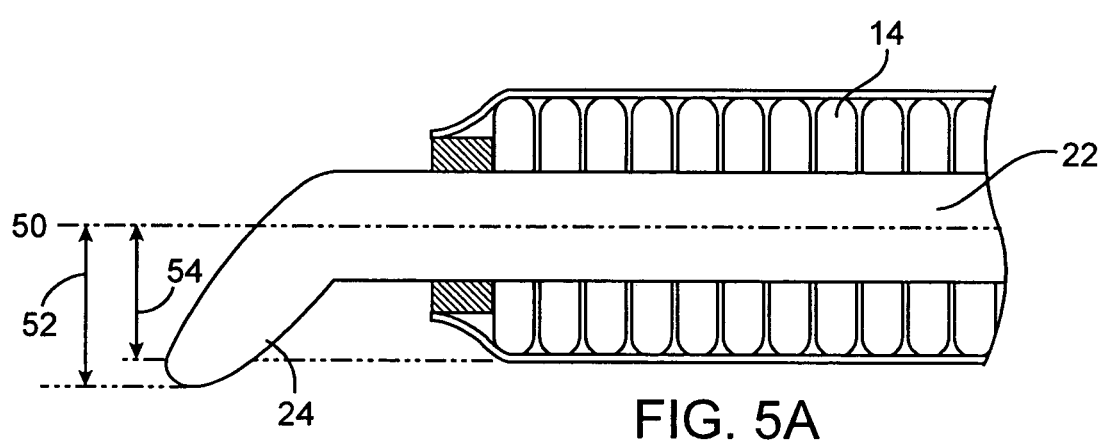
FIG. 5A shows a deflected distal tip in a position forward of the distal end of the elongate member.
Figure 5B:
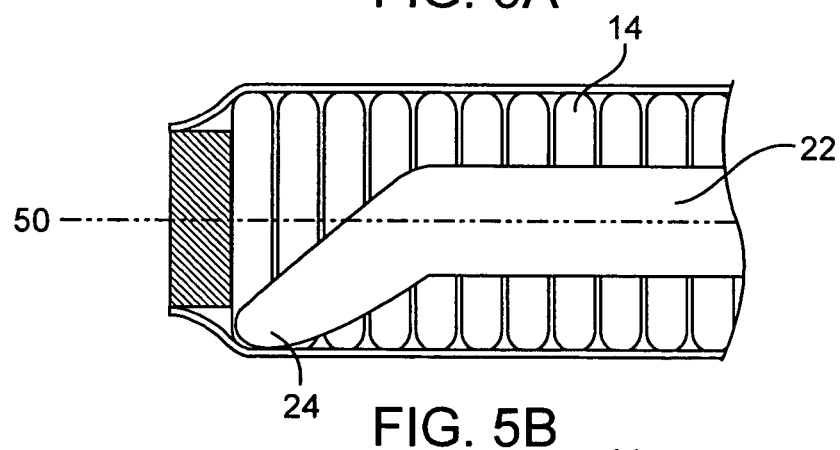
FIG. 5B shows the flexible deflected distal tip in a fully retracted position within the axial lumen of the elongate member.
Figure 5C:
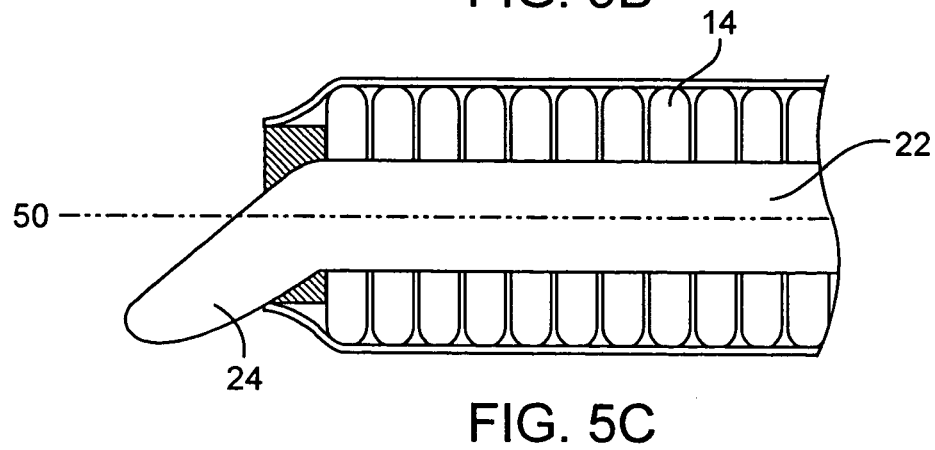
FIG. 5C shows a deflected distal tip in a retracted position with the distal tip partially extending out of the elongate member.

As shown in FIGS. 4 and 5A-5C, the distal tip can be shaped or deflected from the longitudinal axis 50 to extend beyond the radius of the elongate member 14 such that rotation of the drive shaft 22 creates a path radius 52 that is as at least as large as the radius 54 of the distal end of the elongate member 14. In other embodiments, the distal tip 24 will be deflected and shaped so as to create a path radius 52 which is the same or smaller than the radius of the distal end of the elongate member 14 (FIGS. 8B-8G). For example, in one exemplary configuration shown in FIG. 5C, a portion of the distal tip 24 extends beyond the distal end 18 of the elongate member when in the fully retracted position. When the drive shaft 22 is advanced out of the elongate member 14, the flexible distal tip 24 maintains a deflected shape (FIG. 5A). In alternative configurations, it is contemplated that the deflection at the distal tip 24 can straighten somewhat under the force from the walls of the elongate member 14 when the drive shaft 22 is retracted into the elongate member 14 (FIG. 5B). Thus, in the axially retracted configuration, the drive shaft 22 will have a profile that is smaller than the radius of the distal tip of the elongate member. When the drive shaft is advanced out of the distal end of the elongate member, the drive shaft will expand to an axially extended configuration in which the distal tip of the drive shaft 22 will have a profile that is larger than the axially retracted configuration, and in some embodiments will have a larger profile than the distal end of the elongate member 14.

Referring again to FIG. 4, in some configurations a layer of abrasive material 56 can be attached and distributed over at least a portion of the distal tip 24 of the drive shaft 22 so that the abrasive material 56 engages the stenotic or occlusive material as the drive shaft 22 is advanced into the occlusion or stenosis. The abrasive material 56 can be diamond powder, diamond chips, fused silica, titanium nitride, tungsten carbide, aluminum oxide, boron carbide, or other conventional abrasive particles.

Figure 6A:
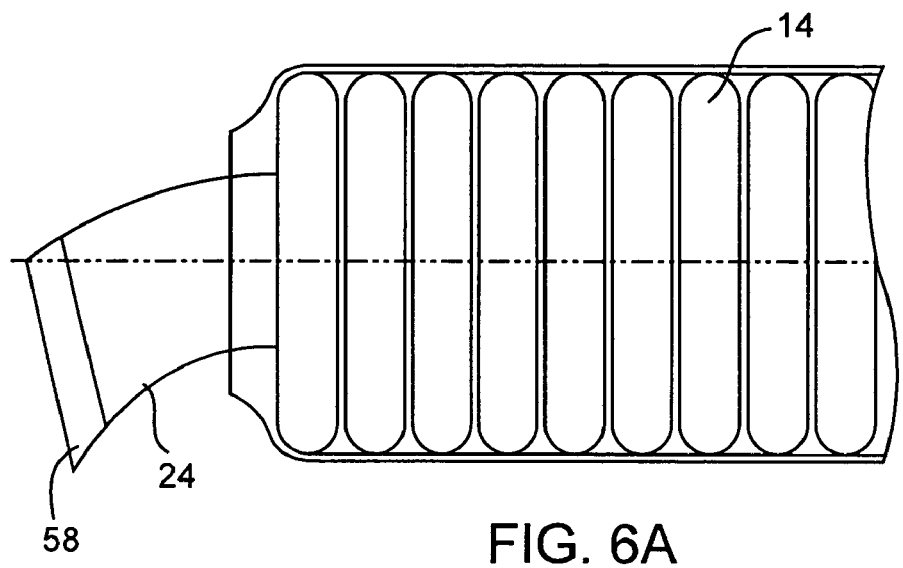
FIG. 6A shows a sharpened deflected distal tip extending out of the elongate member.
Figure 6D:
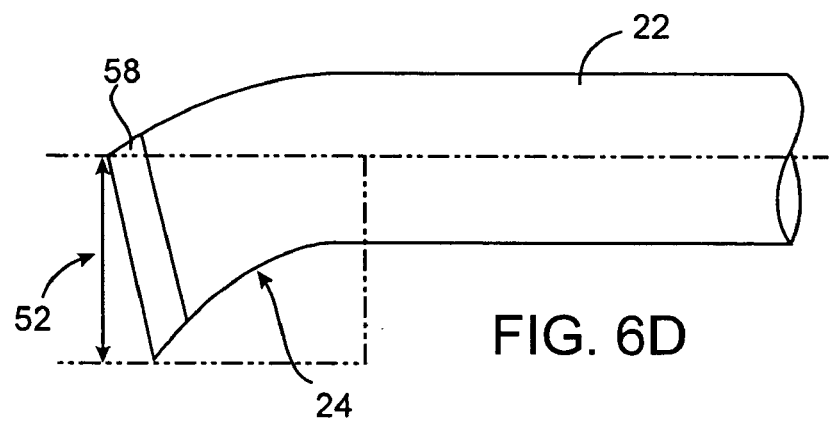
FIG. 6D shows the distal tip deflected off of the longitudinal axis of the drive shaft.
Figure 6B:
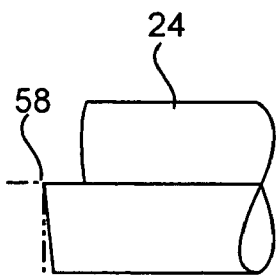
FIGS. 6B and 6C show the cutting edges on the deflected distal tip of FIG. 6A.
Figure 6C:
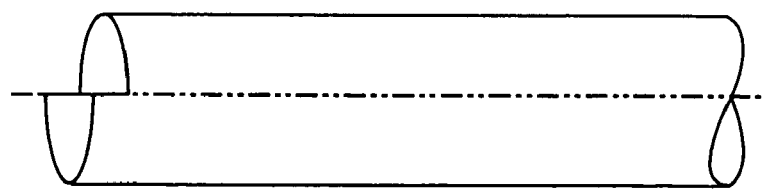

Alternatively, as shown in FIGS. 6A-6D, the distal tip 24 of the drive shaft 22 can be sharpened to facilitate passing through the occlusion or stenosis. A distal edge of the tip 24 can be sharpened so as to define a cutting edge 58 which rotatably contacts the occlusive or stenotic material. In an exemplary embodiment illustrated in FIGS. 6B-6C, a tip of the drive shaft can be sharpened to create a plurality of cutting edges 58. Furthermore, as shown in FIG. 6D and as described above, the distal tip 24 can be deflected from its longitudinal axis 50 to create the cutting path radius 52 of the drive shaft 24 that is smaller, larger, or the same length as the radius of the elongate member 14.

Figure 6E:
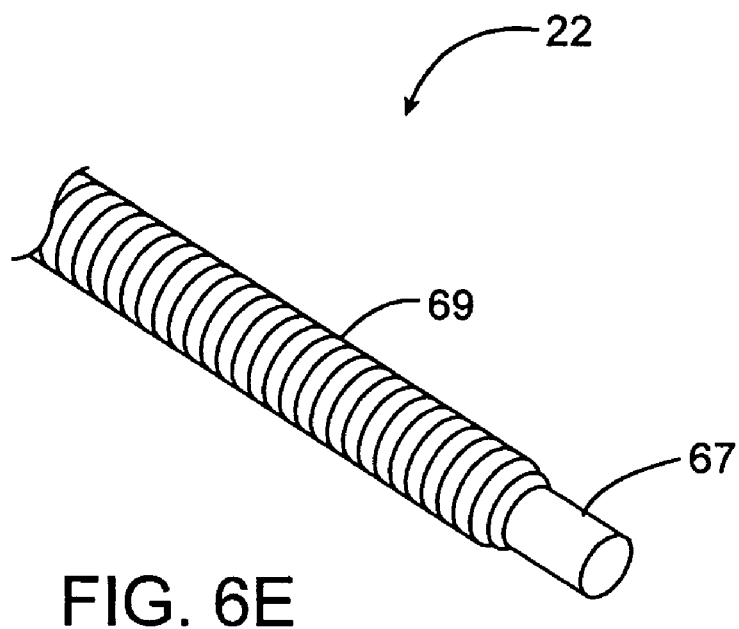
FIGS. 6E and 6F is a partial cut away section of two counter-wound drive shafts of the present invention.
Figure 6F:
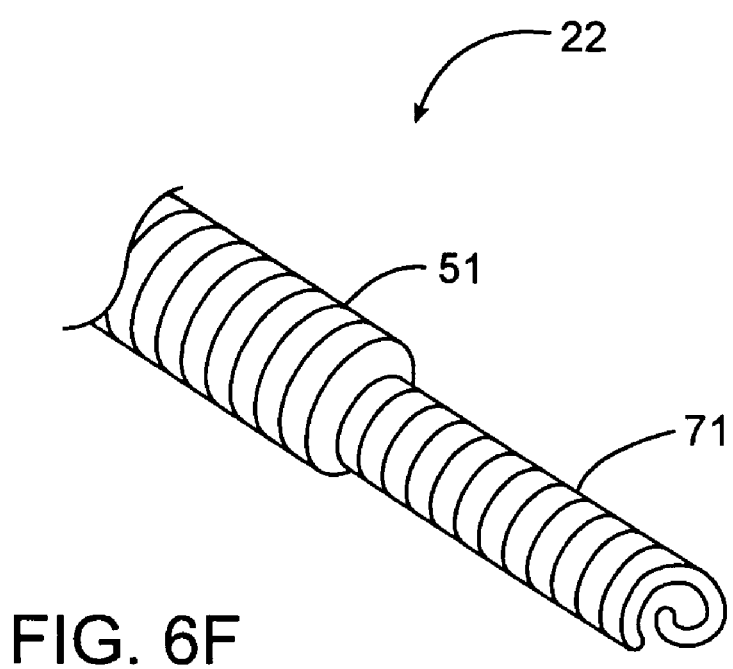

The drive shaft 22 can be composed of a shape retaining material, a rigid material, a flexible material, or can be composed of a plurality of materials. For example in some configurations, the drive shaft 22 can be comprised of nitinol, stainless steel, platinum-iridium, or the like. The distal tip 24 of the drive shaft 22 can have an enlarged tip, a preformed curve, or a preformed deflection (FIG. 5A). FIGS. 6E and 6F show exemplary embodiments of a counter-wound and composite drive shafts of the present invention. The counter-wound drive shaft 22 shown in FIG. 6E is made of a 0.004 inch OD center wire 67 having a right-hand wound surrounding wire 69 coiled around the center wire 67. The surrounding wire 69 can be soldered to the center wire at both ends of the center wire. In the embodiment of FIG. 6F, multiple strand wires 51 can be wound around a central coil 71 to form the drive shaft 22. The counter-wound drive shafts are significantly more flexible than a single wire guidewire and allows for a tighter bending radius over conventional guidewire. FIG. 6G illustrates the flexibility of both a 0.007 inch OD single wire stainless steel wire drive shaft 22a and a 0.007 inch OD counter-wound stainless steel drive shaft 22b. As shown by FIG. 6G, the counter-wound drive shaft has better flexibility, while still maintaining its torqueability, maneuverability, and columnar strength.

Additionally, in some embodiments, the distal portion of the drive shaft 22 is radiopaque so that a physician can track the position of the drive shaft 22 using fluoroscopy. The drive shaft 22 typically has a diameter between approximately 0.010 inches and 0.005 inches. It should be appreciated that the dimension of the drive shaft will be slightly less than the inner diameter of the hollow guidewire so as to allow rotation without significant heat generation. Consequently, the dimensions of the drive shaft will vary depending on the relative inner diameter of the elongate member 14 and the present invention is not limited to the above described dimensions of the drive shaft.

Figure 7A:
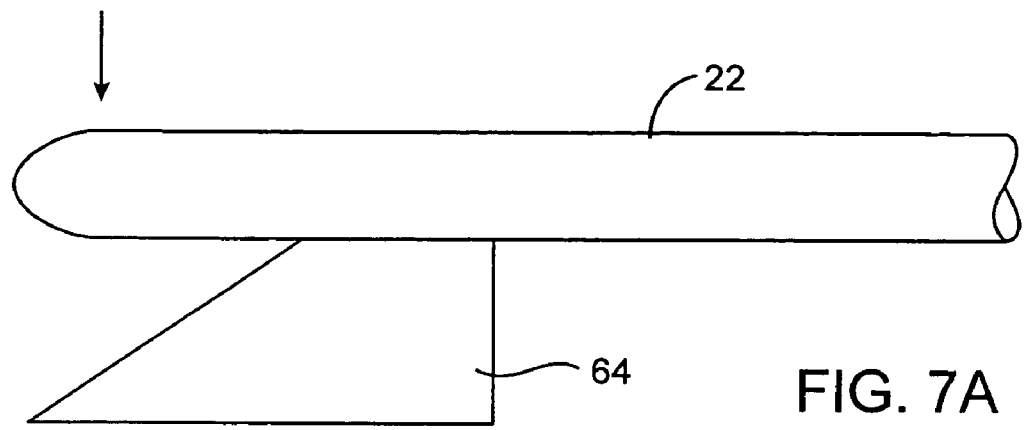
FIGS. 7A to 7C illustrate a method of forming the deflected distal tip using a fixture.
Figure 7B:
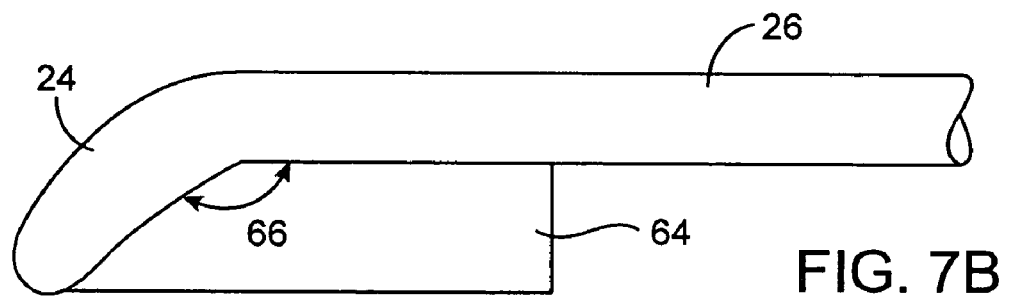
Figure 7C:
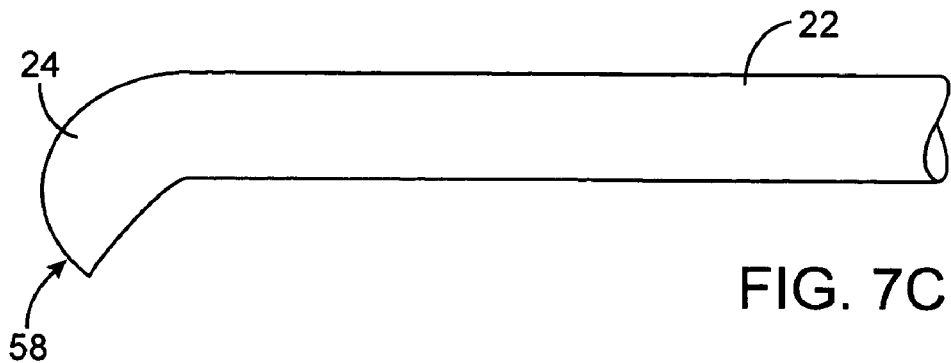

In one embodiment, the distal tip 24 of the drive shaft is created using a shaped fixture 64. As shown in FIGS. 7A and 7B, the distal tip 24 is positioned on the fixture 64 and bent to a desired angle 66. The distal tip 24 can be bent to almost any angle 66 between 0° degrees and 90° degrees from the longitudinal axis 50, but is preferably deflected between 0° degrees and 50° degrees. As shown in FIG. 7C, a sharpened edge 58 can be created on the distal tip using a wafer dicing machine used in the production of silicon microchips (not shown). The angle of the sharpened edge 58 can be almost any angle, but the angle is typically between 0° degrees and 45° degrees, and is preferably between approximately 8° degrees and 18° degrees. Naturally, it will be appreciated that a variety of methods can be used to manufacture the distal tip of the drive shaft and that the present invention is not limited to drive shafts produced by the described method.

Figure 8A:
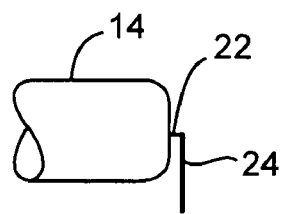
FIGS. 8A-8K show a variety of tip configurations.
Figure 8D:
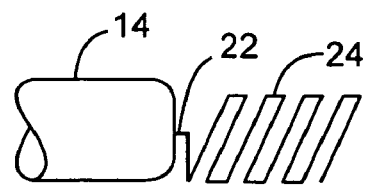
Figure 8B:
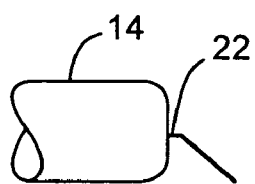
Figure 8E:
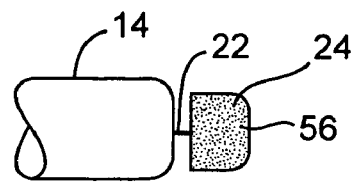
Figure 8C:
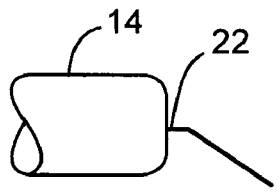
Figure 8F:
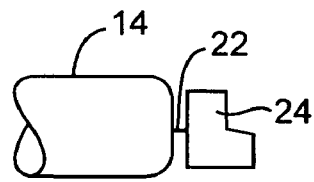
Figure 8G:
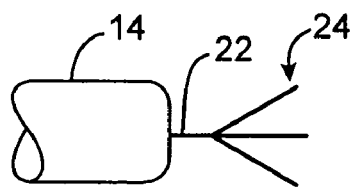

As mentioned above, the distal tip 24 can take various shapes. One embodiment having a deflected distal tip 24 is shown in FIG. 8A. In an exemplary configuration, the deflected tip is offset at an angle such that rotation of the drive wire 22 defines a profile or path that is at least as large as the outer diameter of the distal end of the elongate member 14. As shown in FIGS. 8B and 8C, in other embodiments, the tip can be deflected at other angles and may have a length that creates a path that is smaller or the same diameter as the distal end of the elongate member. The deflected distal tip can extend radially any feasible length beyond the perimeter or diameter of the elongate member 14. It should be understood that the invention is not limited to a single deflected tip. For example, the drive shaft can comprise a plurality of deflected tips. Alternatively, the drive shaft may have a distal tip 24 that is twizzle shaped, spring shaped, twisted metal shaped (FIG. 8D), ball shaped (FIG. 8E), a discontinuous surface (FIG. 8F), or the like. Alternatively, the drive shaft may comprise a plurality of filaments (FIG. 8G), rigid or flexible brush elements, a plurality of coils, or the like.

Figure 8H:
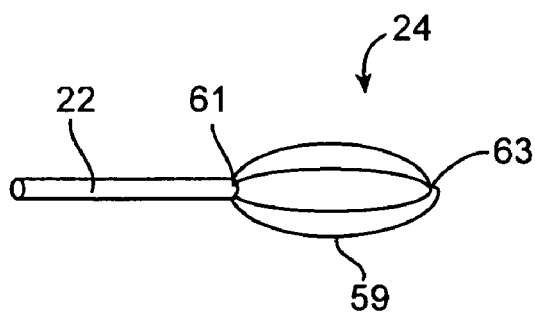
Figure 8I:
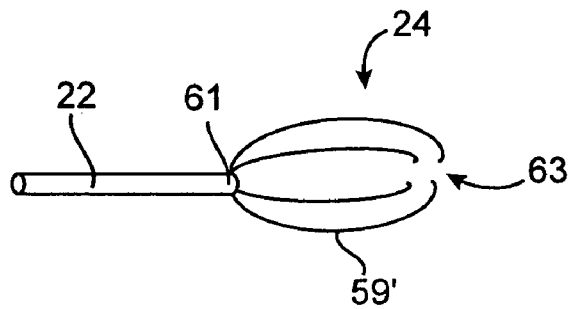
Figure 8J:
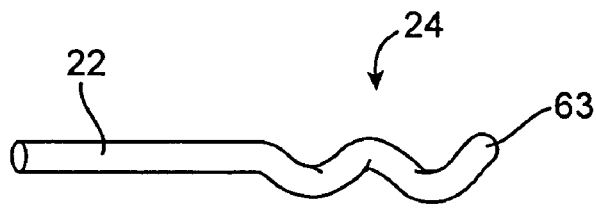
Figure 8K:
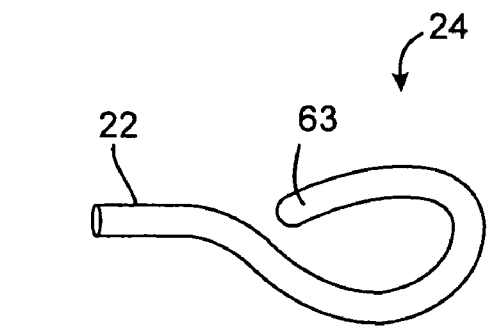

The distal tip of the drive shaft can be configured optimally for the type of occlusion or stenosis to be penetrated. Some lesions are made up substantially of clot or thrombotic material that is soft and gelatinous. FIGS. 8H and 8K shows distal tip embodiments which may be used to macerate a soft clot, thrombotic material, or stenosis. FIG. 8H shows a distal tip 24 having a basket like construction which is made up of a plurality of strands 59 that are connected at their ends 61, 63. In another embodiment illustrated in FIG. 8I, the distal tip 24 can be composed of a plurality of strands 59 that are unconnected at their distal ends 63. Additionally, the distal ends 63 of the strands 59 can be turned inward so that the distal ends 63 do not penetrate the body lumen when rotated. FIG. 8J shows a corkscrew spiral distal tip having a blunt distal end 63. FIG. 8K shows a distal tip having a loop configuration.

In use, the distal tip 24 is rotated and advanced distally from a retracted position to an expanded position into the soft material in the target lesion. If slow speed rotation is desired the user can rotate the drive shaft slowly by hand by grasping a knurled knob attached to the proximal end of the drive shaft (FIG. 1B). If high speed rotation is desired, the proximal end of the drive shaft 22 can be attached to the drive motor 26. As the expanded wire basket tip is rotated, the tip macerates the soft clot and separates the clot from the wall of the body lumen. If a large diameter hollow guidewire working channel is used to deliver the drive shaft to the target area, the macerated clot can be aspirated through the guidewire working channel. Alternatively or additionally, a fluid, such as thrombolytic agents, can be delivered through the working channel to dissolve the clot to prevent "distal trash" and blockage of the vasculature with debris from the macerated clot.

Figure 8L:
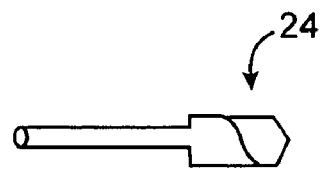
FIG. 8L shows a distal tip having a flattened and twisted configuration.
Figure 8M:
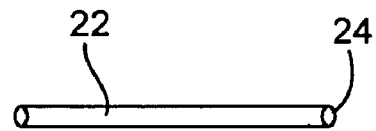
FIGS. 8M-8P show an exemplary method of manufacturing the distal tip of FIG. 8L.

In another exemplary embodiment shown in FIG. 8L, the distal tip 24 of the drive shaft 22 can be flattened and twisted to create a screw lie tip that can create a path through the occlusion. The flattened and twisted distal tip 24 can have a same width, a smaller width or a larger width than the drive shaft 24. For example, in one configuration for a drive shaft having an outer diameter of 0.007 inches, the distal tip 24 can be flattened to have a width between approximately 0.015 inches and 0.016 inches, or more. It should be appreciated, however, that the distal tip can be manufactured to a variety of sizes.

Figure 8N:
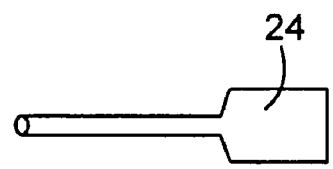
Figure 8O:
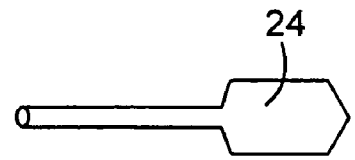
Figure 8P:

FIGS. 8M-8P show one method of manufacturing the flattened and distal tip of the present invention. The round drive shaft 22 (FIG. 8M) is taken and the distal end is flattened (FIG. 8N). The distal end can be sharpened (FIG. 8O) and twisted two or two and a half turns (FIG. 8P). If a different amount of twists are desired, the distal tip can be manufactured to create more (or less) turns.

Figure 9:
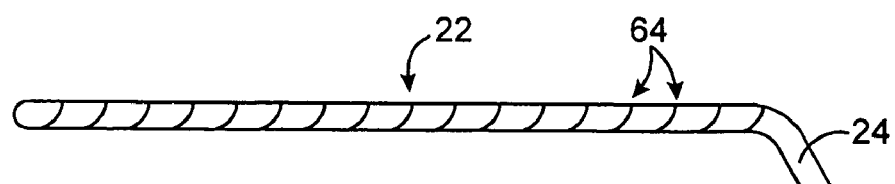
FIG. 9 shows a drive shaft having spirals or external riflings which facilitate the proximal movement of the removed occlusive or stenotic material.
Figure 15:
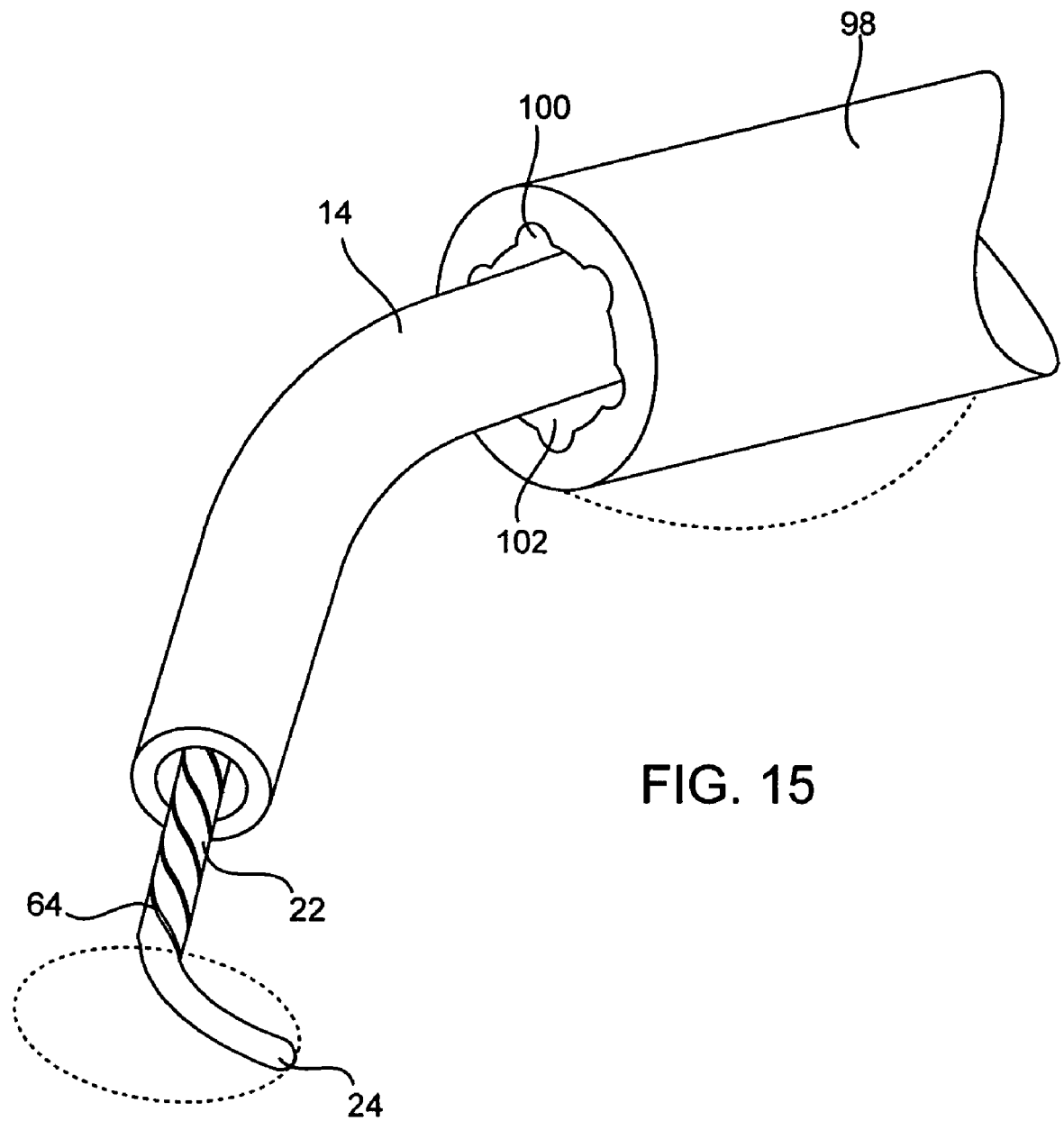
FIG. 15 shows a system having an access system, a hollow guidewire with a deflectable distal end, and a drive shaft.

As shown in FIGS. 9 and 15 in some embodiments the drive shaft 22 can optionally have spiral threads or external riflings 64 which extend along the body 44. As the drive shaft 22 is rotated and axially advanced into the atheromatous material, the distal tip 24 creates a path and removes the atheromatous material from the blood vessel. The rotating spirals 64 act similar to an "Archimedes Screw" and transport the removed material proximally up the axial lumen of the elongate member 14 and prevent the loose atheromatous material from blocking the axial lumen of the elongate member 14 or from escaping into the blood stream.

In use, drive shaft 24 is rotated and advanced to create a path distal of the elongate member 14 to create a path through the occlusion. The drive shaft 24 can be advanced and rotated simultaneously, rotated first and then advanced, or advanced first and then rotated. The drive shaft 22 is typically ramped up from a static position (i.e. 0 rpm) to about 5,000 rpm, 20,000 rpm with a motor. It should be noted, however, that the speed of rotation can be varied (higher or lower) depending on the capacity of the motor, the dimensions of the drive shaft and the elongate member, the type of occlusion to be bypassed, and the like. For example, if desired, the drive shaft can be manually rotated or reciprocated at a lower speed to macerate soft clots or to pass through lesions.

The distal tip of the drive shaft 22 can extend almost any length beyond the distal portion of the hollow guidewire. In most embodiments, however, the distal tip typically extends about 5 centimeters, more preferably from 0.05 centimeters to 5 centimeters, and most preferably between 0.05 centimeter and 2 centimeters beyond the distal portion of the hollow guidewire.

Figure 10:
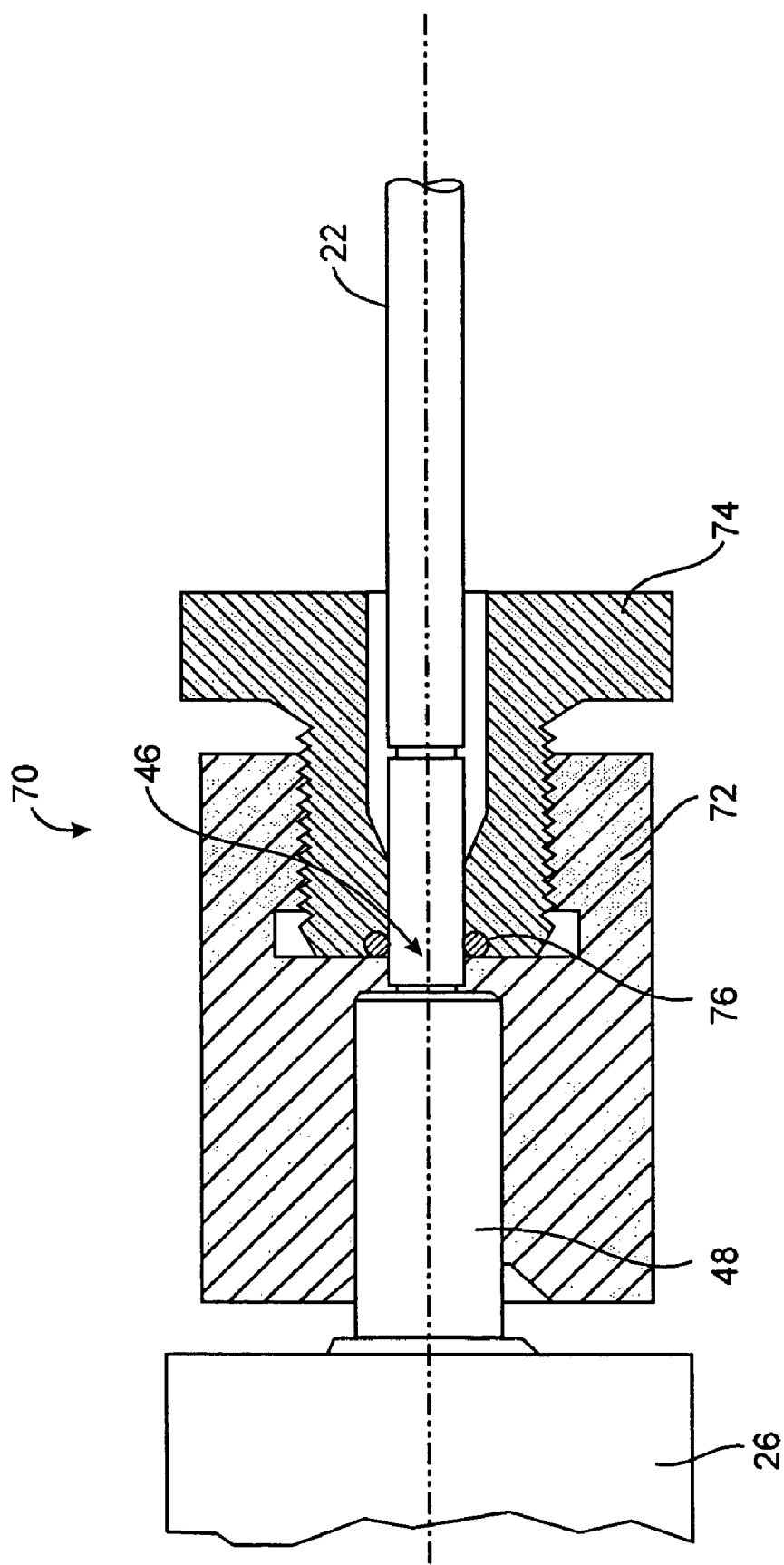
FIG. 10 shows a linkage assembly between the motor shaft and the drive shaft.
Figure 11A:
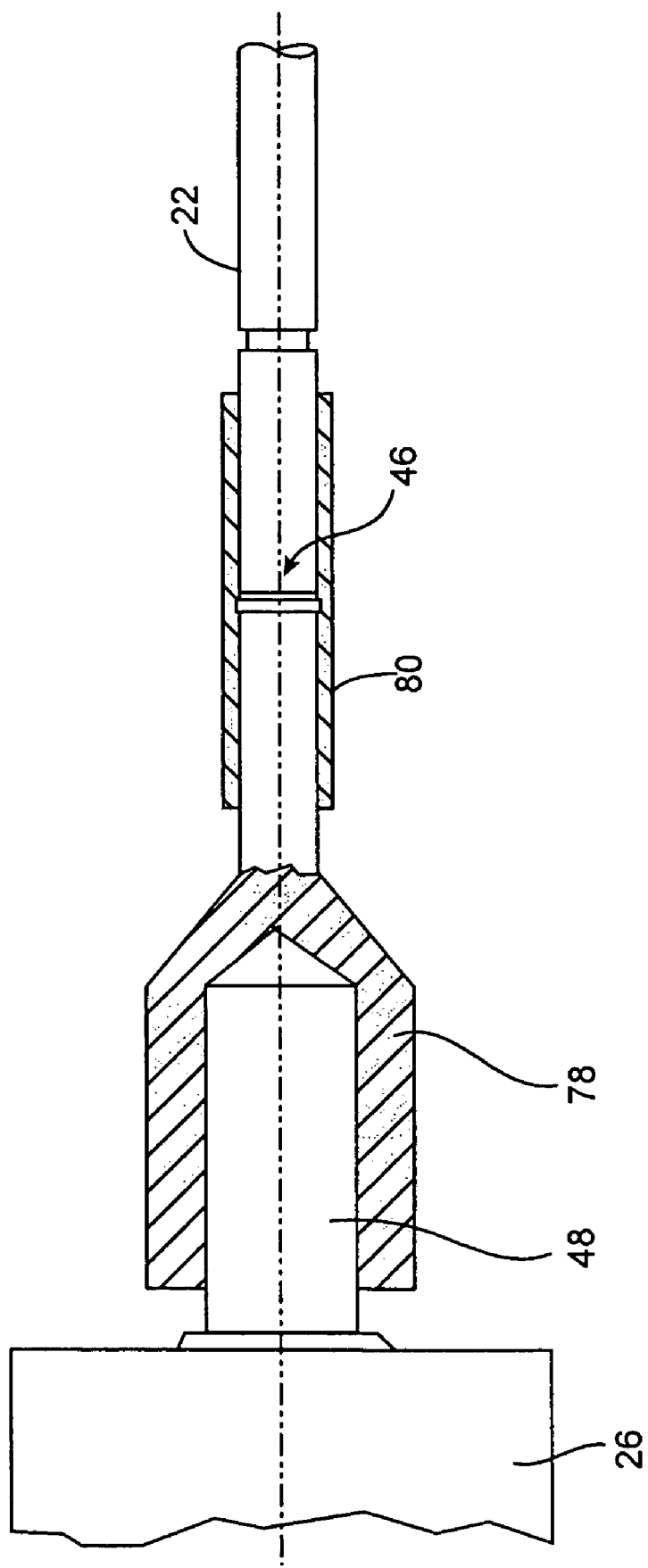
FIGS. 11A and 11B show an alternative linkage assembly coupling the motor shaft and the drive shaft.
Figure 11B:
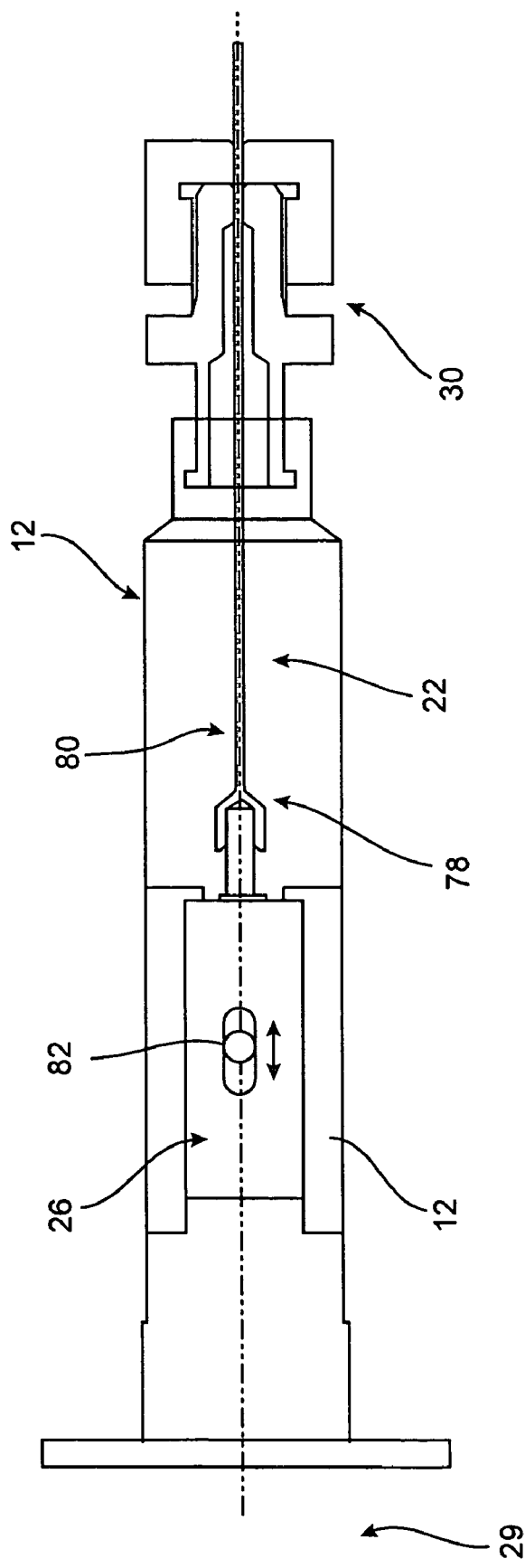

Referring now to FIGS. 10, 11A, and 11B, the motor shaft 48 and the proximal end 46 of the drive shaft 22 are coupled together with a detachable linkage assembly 70. In one embodiment shown in FIG. 10, linkage assembly 70 has a first flange 72 attached to the motor shaft 48. The first flange can be snap fit, snug fit, or permanently attached to the drive shaft 48. A second flange 74 can be permanently or removably coupled to the proximal end 46 of the drive shaft 22 so that the first flange 72 of the motor shaft 48 can threadedly engage the second flange 74. In some embodiments, the proximal end of the drive shaft 46 can be enlarged so as to improve the engagement with the second flange 74. An o-ring 76 is preferably disposed within a cavity in the first flange 72 to hold the first flange 72 and second flange 74 in fixed position relative to each other.

As shown generally in FIGS. 1A and 11B, the motor 26 can be removably coupled to the housing 12. To detach the motor 26 and power supply 28 from the drive shaft 22, the user can unlock the luer assembly 30 so as to release the elongate member 14 from the housing 12. The drive shaft 22 and elongate member 14 are then both free to move axially. The motor 26 can be moved proximally out of the housing 12 and the proximal end 46 of the drive shaft 22 can be detached from the motor shaft 48. After the motor 26, housing 12, and luer assembly 30 have been uncoupled from the elongate member 14 and drive shaft 22, a support or access system (not shown) can be advanced over the free proximal end of the elongate member 14. Thereafter, the luer assembly and motor shaft 48 can be recoupled to the elongate member 14.

In the embodiment shown in FIGS. 11A and 11B, the linkage assembly 70 includes a connecting shaft 78 that can be snugly fit over the motor shaft 48. The connecting shaft 78 preferably tapers from a diameter slightly larger than the motor shaft 48 to a diameter of that of the approximately the proximal end 46 of the drive shaft 22. In the embodiment shown, the connecting shaft 78 is coupled to the drive shaft through shrinkable tubing 80. Because the connecting shaft 78 is snug fit over the motor shaft, (and is not threadedly attached to the drive shaft) the size of the connecting shaft 78 can be smaller than the linkage assembly 70. While the exemplary embodiments of the connection assembly between the drive shaft and motor shaft have been described, it will be appreciated that drive shaft and motor shaft can be attached through any other conventional means. For example, the motor shaft 48 can be coupled to the drive shaft 22 through adhesive, welding, a snap fit assembly, or the like.

As shown in FIG. 11B, the drive shaft 22 extends proximally through the housing 12 and is coupled to the motor shaft 48. An actuator 82 can be activated to advance and retract the drive shaft 22. In some embodiments, the motor is press fit into the actuator housing 12. The drive shaft 22 is attached to the motor shaft 26 via o-rings such that the drive shaft 22 can be moved axially through axial movement of the actuator 82.

In most embodiments, actuation of the drive motor 26 and power supply 28 (e.g. rotation of the drive shaft) will be controlled independent from advancement of the drive shaft 22. However, while the actuator 82 is shown separate from the control system 27 and power supply 28 (FIG. 1A), it will be appreciated that actuator 82 and control system 27 can be part of a single, consolidated console attached to the housing 12 or separate from the housing 12. For example, it is contemplated that the drive shaft 22 can be rotated and advanced simultaneously by activation of a single actuator (not shown).

A connection assembly 30 is positioned on a proximal end of the housing to couple the hollow guidewire 14 and the drive shaft 22 to the housing 12. In a preferred embodiment shown in FIGS. 12-14, the connection assembly 30 is a detachable luer which allows the drive shaft 22 to be moved (e.g. rotated, reciprocated, translated) while the elongate member is maintained in a substantially static position. FIG. 12 best illustrates an exemplary luer connection assembly 30 which couples the elongate member 14 and the housing 12. The luer has a gland 86 which is rotatably connected to a fitting 88 and a tubular portion 90. Rotation of the gland 86 rotates and torques the elongate member 14 while the elongate member 14 is advanced through the blood vessel. Fitting 88 is threaded into the gland 86 such that a distal end of the fitting engages an o-ring 92 and a surface wall 94 of the gland. The longitudinal axis 96 of the fitting 88 and gland 86 are aligned so as to be able to receive the axial lumen of the elongate member 14. As the fitting 88 engages the o-ring 92, the o-ring is compressed radially inward to squeeze and maintain the position of the elongate member 14. Accordingly, as illustrated in FIG. 13, when the drive shaft 22 is rotated within the elongate member 14, the o-ring 92 is able to substantially maintain the position and orientation of the elongate member 14. Tubular portion 90 attached to the proximal end of the fitting 88 threadedly engages the housing 12 and enables the luer connection assembly 30 to be removed from the housing 12 (FIG. 14). A more complete description of the connection assembly 30 can be found in commonly owned U.S. patent application Ser. No. 09/030,657, filed Feb. 25, 1998, the complete disclosure of which was previously incorporated by reference. It should be appreciated that the present invention is not limited to the specific luer assembly described. Any luer assembly can be used to connect the elongate member 14 to the housing 12. For example, a Y-luer assembly (not shown) can be used with the system of the present invention to infuse or aspirate of fluids through the lumen of the hollow guidewire 14.

As shown in FIG. 15, systems of the present invention can further include an access or support system 98. The access or support system 98 can be an intravascular catheter such as a hollow guidewire support device, support catheter, balloon dilation catheter, atherectomy catheters, rotational catheters, extractional catheters, conventional guiding catheters, an ultrasound catheter, a stenting catheter, or the like. In an exemplary configuration shown in FIG. 15, the system includes an infusion or aspiration catheter which has at least one axial channel 100, and preferably a plurality of axial channels 100 which extends through the catheter lumen 102 to the distal end of the catheter. The elongate member 14 and drive shaft 22 can be positioned and advanced through the lumen 102 of the catheter. The axial channel 20 of the elongate member 14 and/or the axial channels 100 of the catheter 98 can also be used to aspirate the target site or infuse therapeutic, diagnostic material, rinsing materials, dyes, or the like.

Figure 16A:
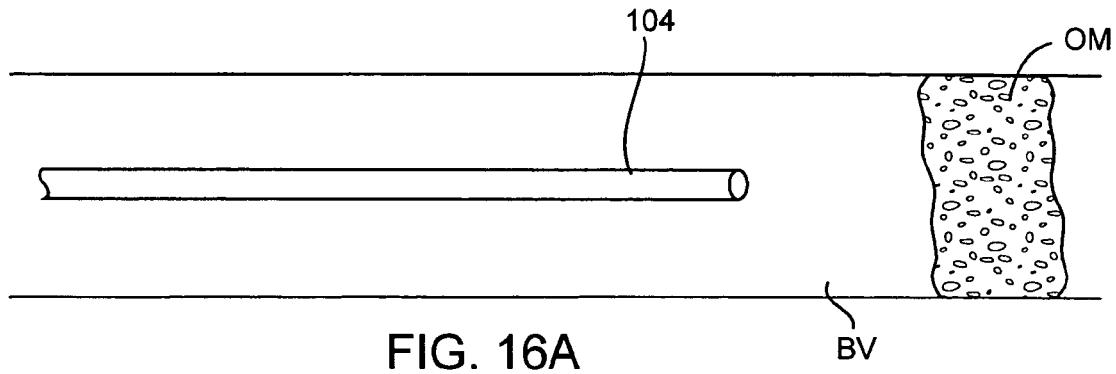
FIGS. 16A to 16E illustrate a method of the present invention.
Figure 16B:
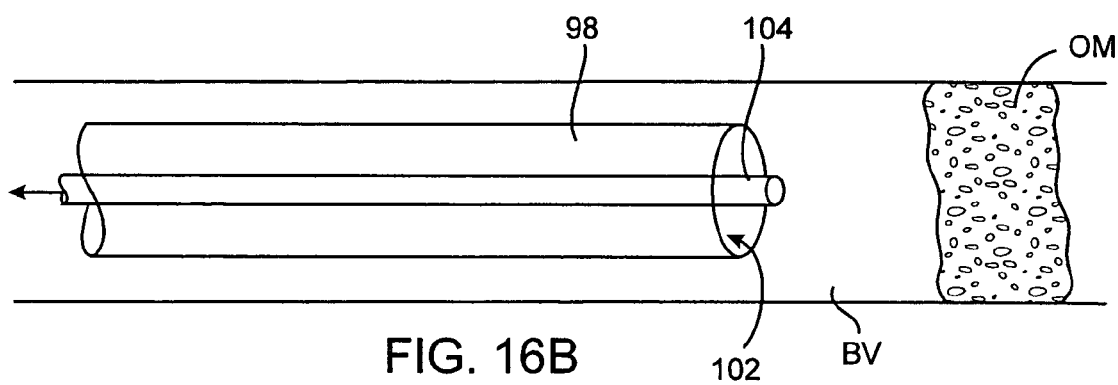
Figure 16C:
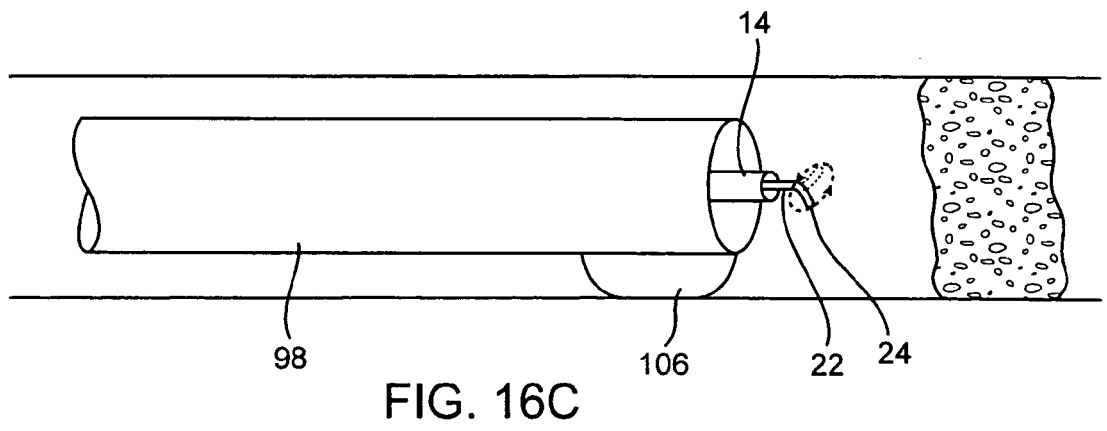
Figure 16D:
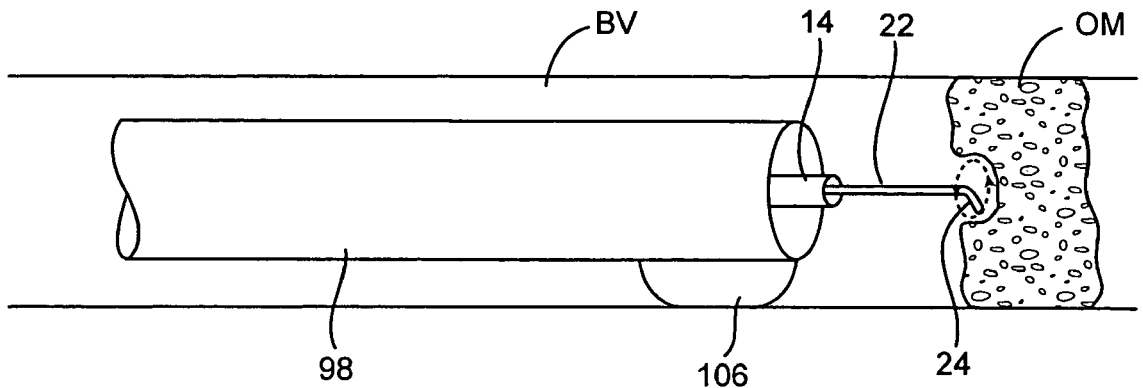
Figure 16E:
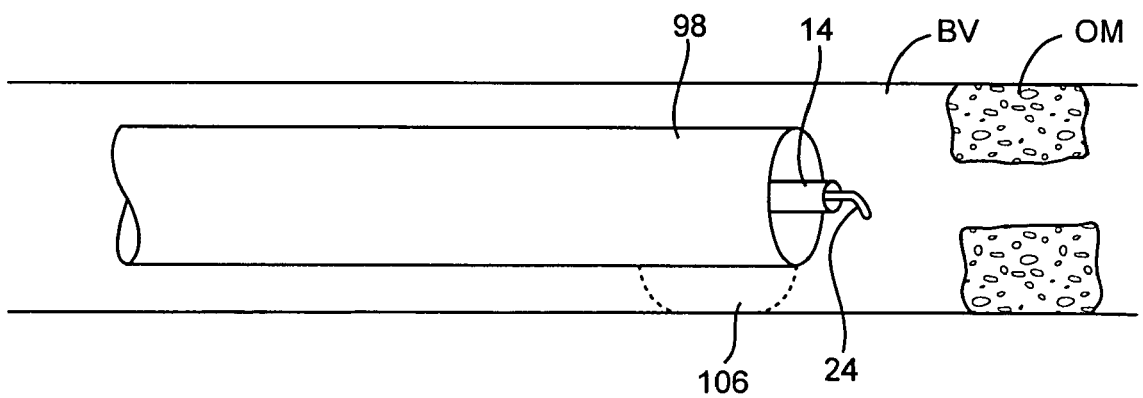

The access or support system can be guided by the elongate member to the target site in a variety of ways. For example, as illustrated in FIGS. 16A to 16E, a conventional guidewire 104 can be advanced through the blood vessel BV from the access site (FIG. 16A). Once the guidewire 104 has reached the target site, the support or access system 98 can be advanced over the guidewire 104 (FIG. 16B). Alternatively, the guidewire 104 and support or access system 98 can be simultaneously advanced through the body lumen (not shown). Once the support or access system 98 has reached the target site, the conventional guidewire 104 can be removed and the hollow guidewire 14 having the drive shaft 22 can be introduced through the lumen 102 of the access system 98 (FIG. 16C). Even if the distal tip 24 of the drive shaft 22 is not fully retracted into the axial lumen 20, the lumen 102 of the support or access system protects the blood vessel BV from damage from the exposed distal tip 22. In most methods, the support or access system is positioned or stabilized with balloons, wires, or other stabilization devices 106 to provide a more controlled removal of the occlusive or stenotic material OM. Once the drive shaft 22 has reached the target site, the drive shaft can be rotated and advanced into the occlusive or stenotic material OM to create a path (FIGS. 16D and 16E).

Figure 17A:
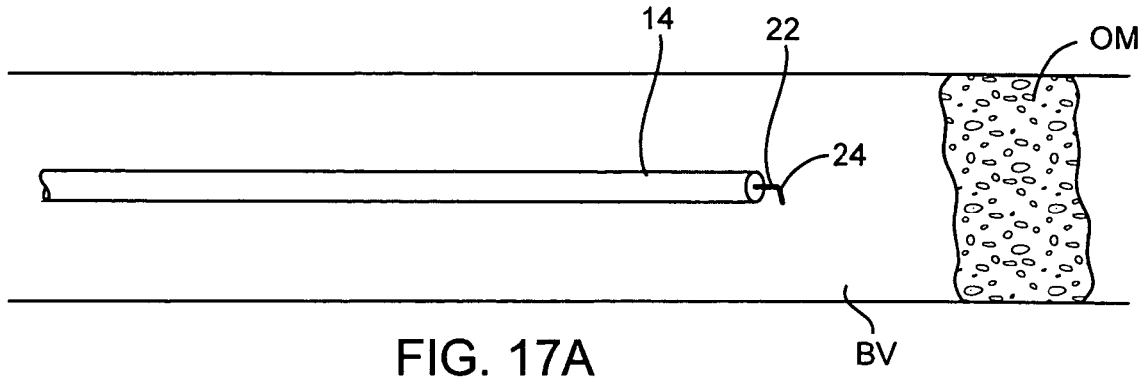
FIGS. 17A to 17E illustrate another method of the present invention.

In another method of the present invention, the hollow guidewire 14 can be used to guide the support or access system to the target site without the use of a separate guide wire. The hollow guidewire 14 provides the flexibility, maneuverability, torqueability (usually 1:1), and columnar strength necessary for accurately advancing through the tortuous vasculature and positioning the distal end of the support or access system at the target site. The steerable distal portion can be deflected and steered through the tortuous regions of the vasculature to get to the target site. As shown in FIG. 17A, the hollow guidewire is advanced through the tortuous blood vessel to the target site. Due to the small size of the guidewire 14 relative to the blood vessel, even if the distal tip 24 of the drive shaft 22 extends partially out of the hollow guidewire 14, any potential damage to the blood vessel BV will be minimal.

Figure 17B:
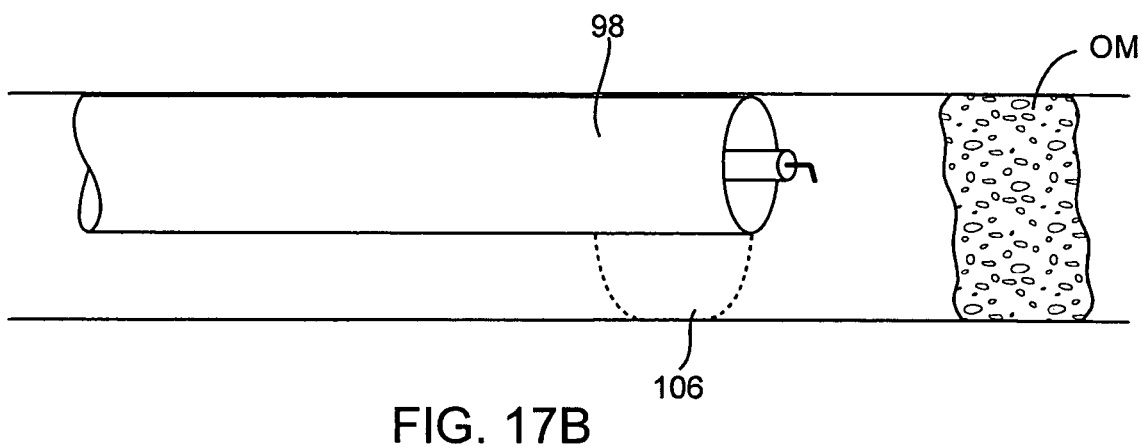
Figure 17C:
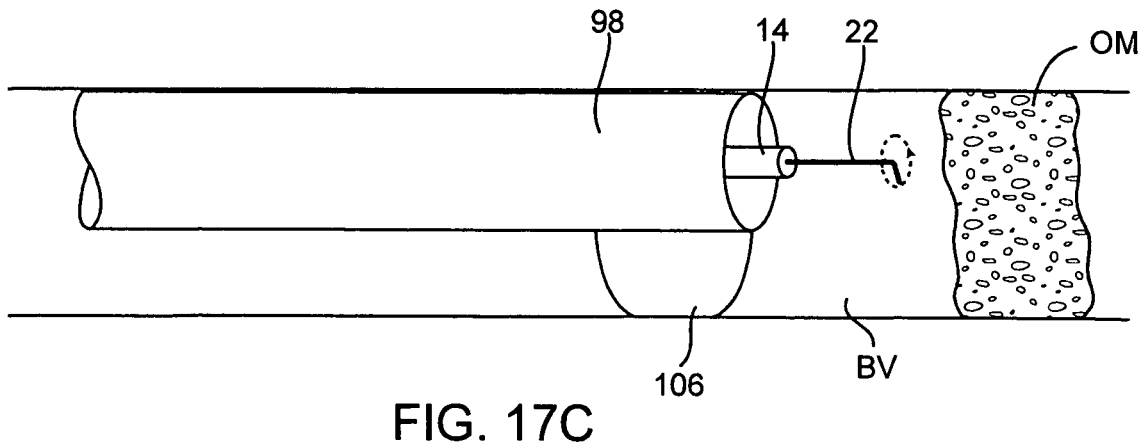
Figure 17D:
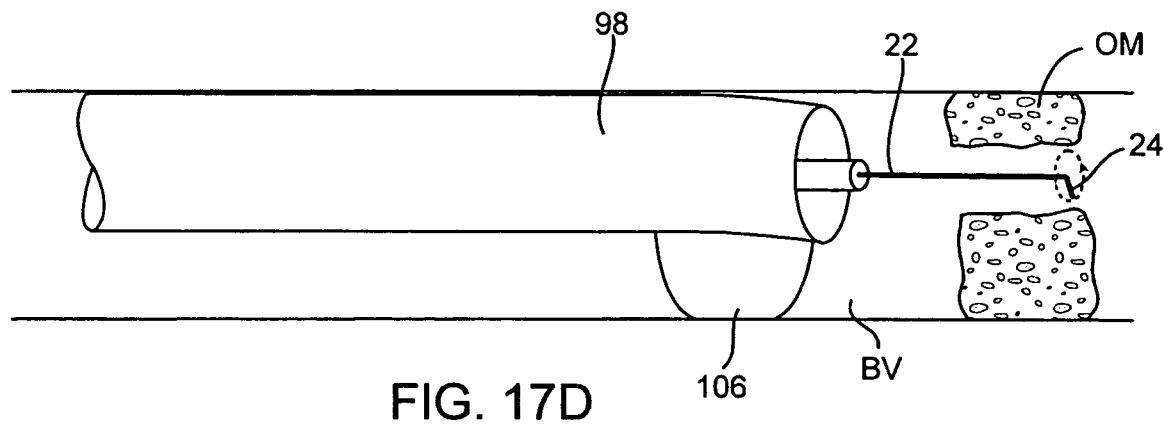
Figure 17E:
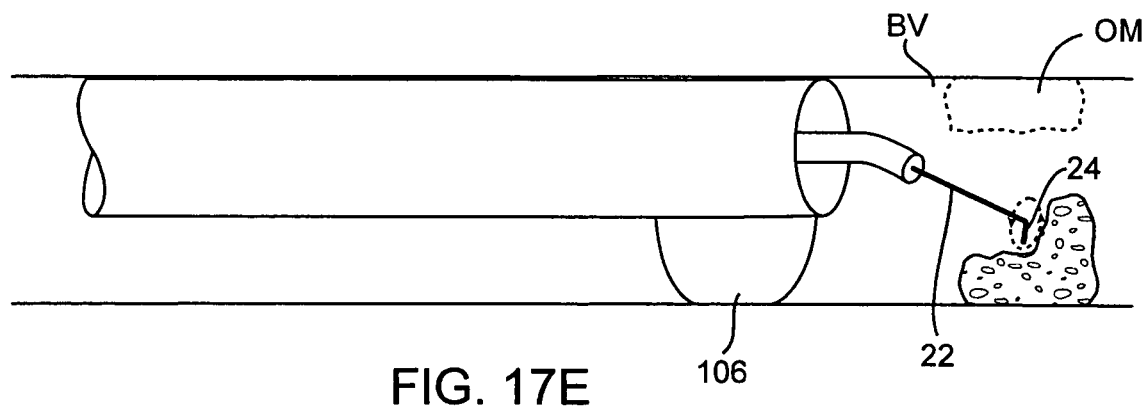

Once the hollow guidewire reaches the target site within the blood vessel, the motor shaft 48, luer assembly 30, and housing 12 can be detached from the proximal end 46 of the drive shaft 22 so that the support or access system can be placed over the hollow guidewire. After the motor has been detached, the support or access system can be advanced over the guidewire and through the body lumen to the target site (FIG. 17B). To reattach the drive motor 26 to the drive shaft 22, the hollow guidewire 14 and drive shaft 22 are inserted through the luer assembly 30. The luer assembly 30 is tightened to lock the position of the hollow guidewire 14. The drive shaft 22 will extend proximally through the housing 12 where it can be recoupled to the motor shaft using the above described linkage assemblies 70 or other conventional linkage assemblies. Once at the target site, the position of the support or access system 98 can be stabilized by a balloon, wires, or other stabilizing devices 106, and the drive shaft 22 can be rotated and advanced into the occlusive or stenotic material OM (FIGS. 17C and 17D). The rotation of the drive shaft creates a path forward of the distal end 18 of the hollow guidewire 14. As noted above, the path can have the same diameter, smaller diameter, or larger diameter than the distal end of the hollow guidewire. Before, during, or after the rotation of the drive shaft, the user can steer or deflect the distal end 18 of the hollow guidewire 14 to guide the hollow guidewire to the desired location within the blood vessel. For example, as shown in FIG. 17E, once a portion of the occlusion or stenosis has been removed, the distal end 18 of the hollow guidewire 14 can be guided to angle the distal end so that the drive shaft is extended into a different portion of the occlusive or stenotic material OM.

Figure 18A:
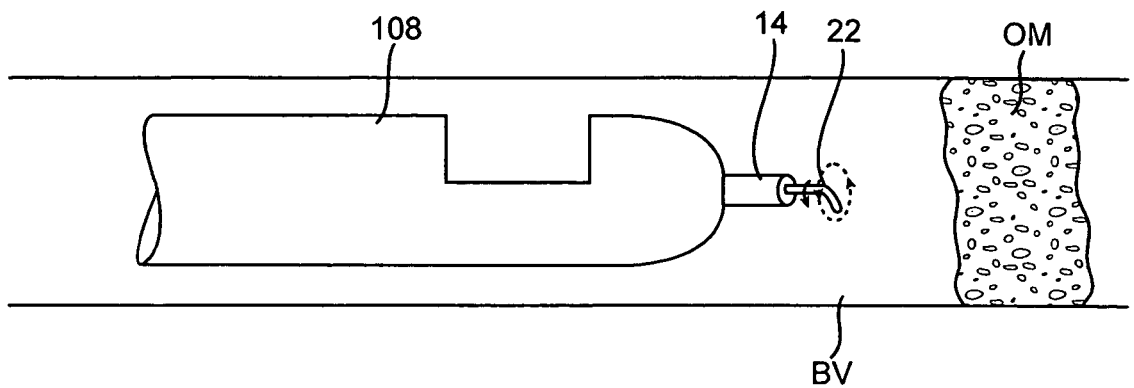
FIGS. 18A to 18B illustrate yet another method of the present invention.
Figure 18B:
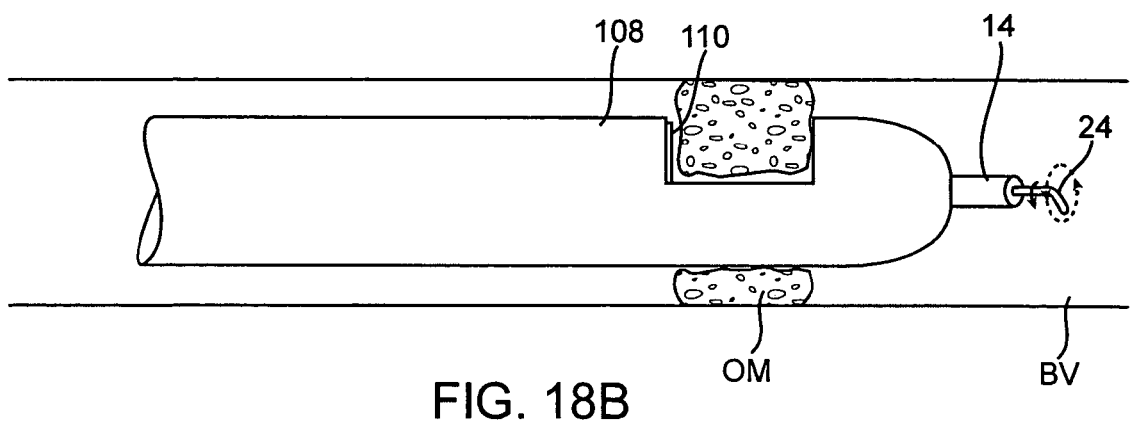

While the apparatus of the present invention is sufficient to create a path through the occlusion OM without the use of a support or access system, the apparatus 10 of the present invention can be used in conjunction with other atherectomy devices to facilitate improved removal or enlargement of the path through the occlusion. For example as shown in the above figures, the hollow guidewire 14 and the atherectomy device 108 can be advanced through the body lumen and positioned adjacent the occlusion OM. The drive shaft 22 is rotated and advanced to make an initial path through the occlusion (FIG. 18A). The hollow guidewire 14 is then moved through the path in the occlusion and the atherectomy device 108 can then be advanced over the hollow guidewire 14 into the path in the occlusion OM to remove the remaining occlusion with cutting blades 110, or the like (FIG. 18B). While FIG. 18B shows cutting blades 110 to remove the occlusive material OM, it will be appreciated that other removal devices and techniques can be used. Some examples include balloon dilation catheters, other atherectomy catheters, rotational catheters, extractional catheters, laser ablation catheters, stenting catheters, and the like.

Figure 19:
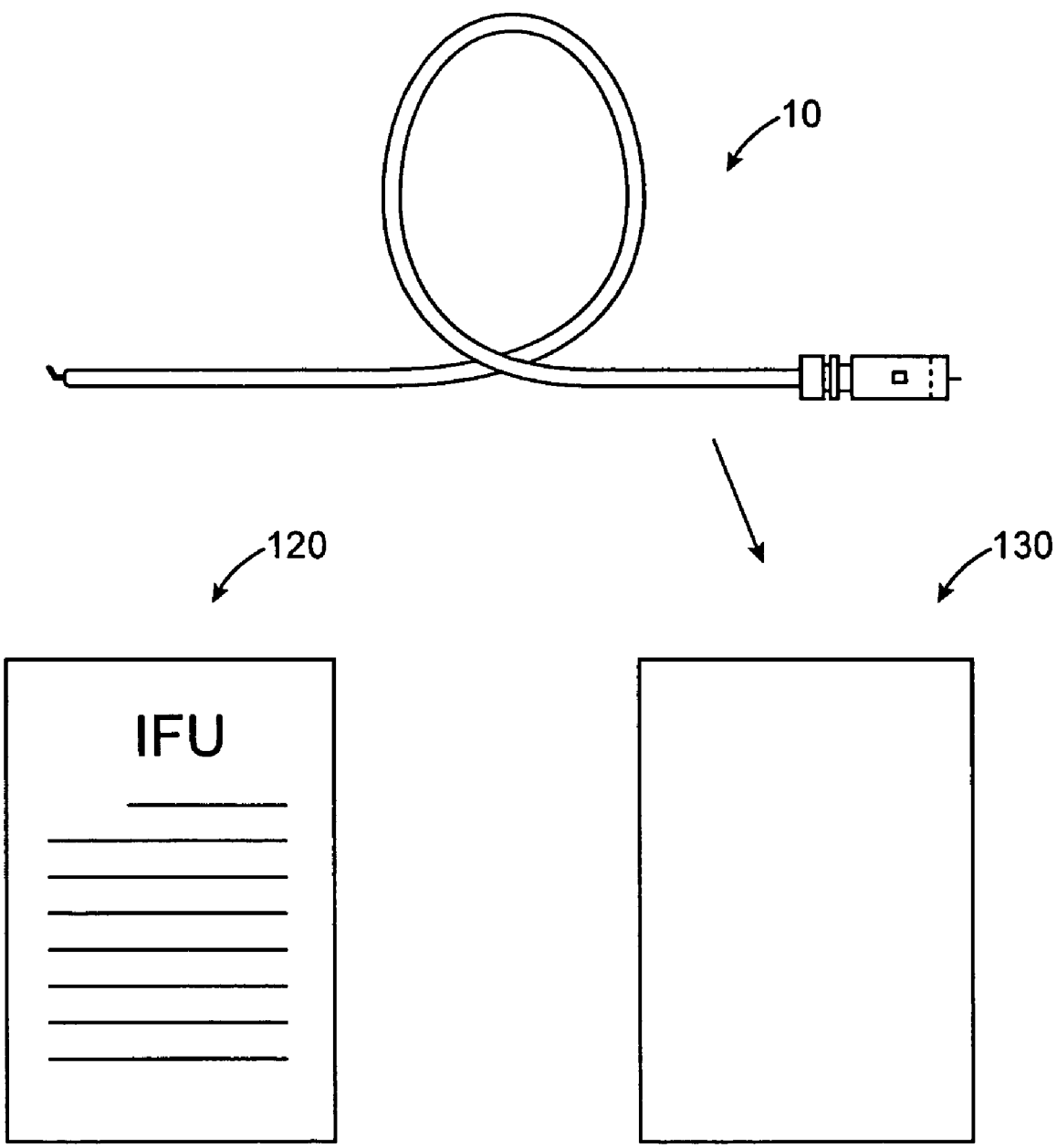
FIG. 19 shows a kit of the present invention.

In another aspect, the invention provides medical kits. As shown in FIG. 19, the medical kit generally includes a system 10, instructions for use (IFU) 120 which describe any of the above described methods, and a package 130. The IFU can be separate from the package or they can be printed on the package. The kits can also optionally include any combination of a second guidewire, a motor, a power supply, a plastic sheath cover, connection assemblies, support or access systems, or the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of crossing an occlusion or stenosis within a blood vessel body lumen comprising:

providing a hollow guidewire having a distal end comprising a coil and a reinforcing wire connected to the coil;

shaping the coil at the distal end of the hollow guidewire, wherein the reinforcing wire retains the coil shape until it is reshaped to a different configuration;

positioning the hollow guidewire into the blood vessel with the shaped distal end thereof on a first side of the occlusion or stenosis, wherein the shaped distal end of the hollow guidewire is maintained and the hollow guidewire is manipulated to navigate the shaped distal end through the blood vessel;

rotating a drive shaft within an inner lumen of the hollow guidewire with a distal tip of the drive shaft extending distally beyond the hollow guidewire, wherein the coil and reinforcing wire retain their shapes while the driveshaft is being rotated; and advancing the rotating distal tip of the drive shaft into the occlusion or stenosis in the blood vessel to create a path through and past the occlusion or stenosis to the other side.

2. The method of claim 1, wherein advancing the distal tip comprises extending the drive shaft from a retracted configuration to an extended configuration.

3. The method of claim 2, wherein the drive shaft is simultaneously extended and rotated.

4. The method of claim 2, wherein the drive shaft is independently extended and rotated.

5. The method of claim 2, wherein the drive shaft in the extended configuration creates a path at least as large as the perimeter of the distal end of the hollow guidewire.

6. The method of claim 2, comprising maintaining a position of the hollow guidewire during the advancing of the distal tip of the drive shaft.

7. The method of claim 1, wherein positioning the hollow guidewire is carried out without the use of a separate guidewire.

8. The method of claim 1, comprising positioning a support system in the body lumen adjacent the occlusion or stenosis, wherein the hollow guidewire is sized to be received within an inner lumen of the support system.

9. The method of claim 8, wherein positioning the support system comprises:

advancing a guidewire through the body lumen to the occlusion or stenosis;

advancing the support system over the guidewire;

removing the guidewire from the body lumen; and advancing the hollow guidewire through the support system.

10. The method of claim 9, comprising infusing or aspirating the body lumen through the inner lumen of the support system.

11. The method of claim 9, comprising maintaining the position of the support system in the body lumen during the advancing of the distal tip.

12. The method of claim 9, comprising using the support system to perform a balloon angioplasty, stent placement, ultrasound, or an atherectomy after the distal tip of the drive shaft has been advanced into the occlusion or stenosis in the body lumen.

13. The method of claim 1, comprising infusing or aspirating the body lumen through the inner lumen of the hollow guidewire.

14. The method of claim 13, wherein the infusing or aspirating is performed simultaneously with the creation of the path in the occlusion or stenosis.

15. The method of claim 13, wherein infusing comprises delivering at least one of a therapeutic material, rinsing material, a dye, and a diagnostic material through the elongate member.

16. The method of claim 1, comprising steering a distal end of the hollow guidewire by actuating a pull wire.

* * * * *